US005567604A

United States Patent [19]
Rando et al.

[11] Patent Number: 5,567,604
[45] Date of Patent: Oct. 22, 1996

[54] ANTI-VIRAL GUANOSINE-RICH OLIGONUCLEOTIDES

[75] Inventors: Robert F. Rando; Susan Fennewald; Joseph G. Zendegui, all of The Woodlands; Joshua O. Ojwang, Spring, all of Tex.

[73] Assignee: Aronex Pharmaceuticals, Inc., The Woodlands, Tex.

[21] Appl. No.: 145,704

[22] Filed: Oct. 28, 1993

Related U.S. Application Data

[63] Continuation-in-part of Ser. No. 53,027, Apr. 23, 1993, abandoned.

[51] Int. Cl.$^6$ ........................................................ C12N 7/06
[52] U.S. Cl. .......................... 435/238; 514/44; 536/23.1; 536/24.1; 536/24.5
[58] Field of Search ............................ 514/44; 536/23.1, 536/24.1, 24.5; 435/238

[56] References Cited

U.S. PATENT DOCUMENTS 5,176,996  1/1993  Hogan et al. ............................ 435/6

FOREIGN PATENT DOCUMENTS 0375408  6/1990  European Pat. Off. .

OTHER PUBLICATIONS

Pharmaceutical Research, vol. 5, No. 9, issued 1988, G. Zon, "Oligonucleotide Analogue as Potential Chemotherapeutic Agents", pp. 539–549.
Biochemie, vol. 67, issued 1985, Miller et al., "Control of Ribonucleic Acid Function by Oligonucleoside Methylphosphonates," pp. 769–776.
Galasso et al., "Antiviral Agents and Viral Diseases of Man," published 1990 by Raven Press, Ltd. (New York), pp. 87–114, see pp. 94–95.
Nucleic Acids Research, vol. 20, No. 2, issued 1992, Zendegui et al, "In Vivo Stability and Kinetics of Absorption and Disposition of 3'-Phosphopropyl Amine Oligonucleotides," pp. 307–314.
Biosis, Abstract No. 94–032,483, issued 1994, Vlassov et al, "The Effect of Modification of Terminal Groups of Oligonucleotides on Their Stability in Mycoplasma Culture," Biopolim. Kletka, vol. 7, No. 5, (Novosibirsk, USSR), pp. 37–41, see abstract.
Nucleic Acids Research, vol. 17, No. 18, issued 1989, Nelson et al., "Bifunctional Oligonucleotide Probes Synthesized Using a Novel CPG Support Are Able to Detect Single Base Pair Mutations," pp. 7187–7194.
Nucleic Acids Research, vol. 17, No. 18, issued 1989, Nelson et al., "A new and Versatile Reagent for Incorporating Multiple Primary Aliphatic Amines Into Synthetic Oligonucleotides," pp. 7179–7186.
B Dropulic et al (1994) Human Gene Therapy 5:927–939.
P A Pizzo et al (1994) Clinical Infections Diseases 19:177–196.
J S Cohen (1992) Trends in Biotechnology 10:87–91.
H Collins (Mar. 6, 1993) Philadelphia Inquirer p. A1.
Sacramento Bee (Feb. 26, 1994) p. A22.
Sacamento Bee (Nov. 29, 1991) p. B5.
Arizona Republic (Nov. 27, 1991) p. A6.
E R Kern (1990) in Antiviral Agents and Viral Diseases of Man, G J Galasso et al, eds, pp. 94–95.
J G Zendegui (1992) Nucleic Acids Research 20:307–314.
V V Vlasov et al (1991) Biopolim Kletka 7:37–41 (Abstract only).

*Primary Examiner*—Bruce R. Campell
*Attorney, Agent, or Firm*—C. Steven McDaniel; Conley, Rose & Tayon, P.C.

[57] ABSTRACT

A method and compositions for treating viral infection in vitro and in vivo using a guanosine-rich oligonucleotides. The oligonucleotides are composed of at least about 50% guanosine nucleotides. Also provided are guanosine-rich oligonucleotides and methods for treating viral infections in humans, and a method for designing guanosine-rich oligonucleotides having anti-viral activity.

12 Claims, 12 Drawing Sheets

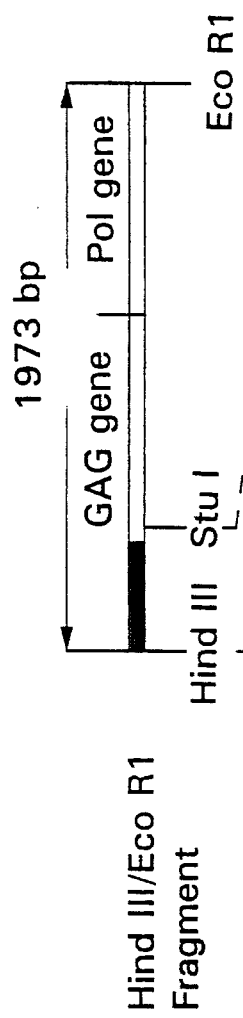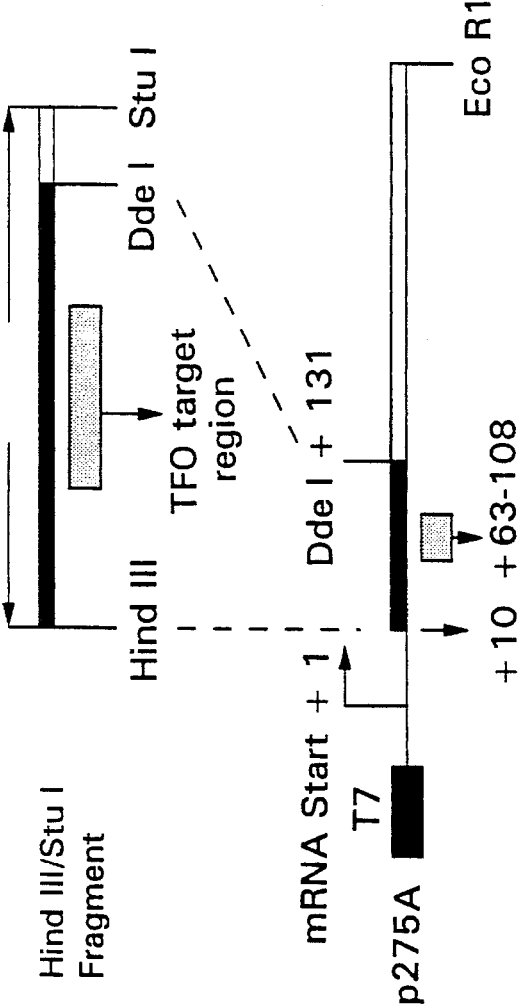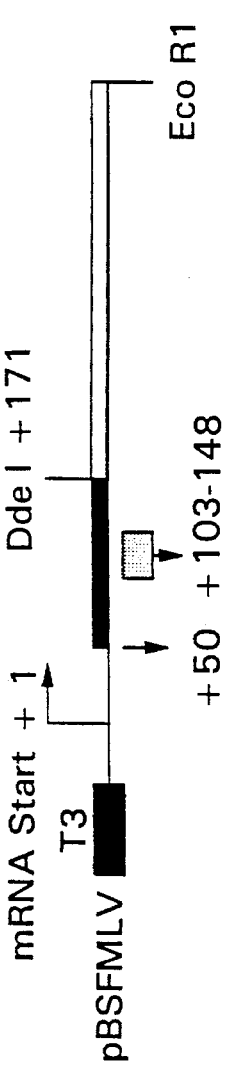
FIG. 1A
FIG. 1B
FIG. 1C
FIG. 1D

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 38
        ( D ) OTHER INFORMATION: /note="Amine moiety attached to 3' end"

( x i ) SEQUENCE DESCRIPTION: SEQ ID NO:1:

```
TGGGTGGGGT GGGGTGGGGG GGTGTGGGGT GTGGGGTG                    38
```

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GTGGGGTGTG GGGTGTGGGG GGGTGGGGTG GGGTGGGT                    38
```

( 2 ) INFORMATION FOR SEQ ID NO:3:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

GGGTGGGTGG GTGGGTGG 18

( 2 ) INFORMATION FOR SEQ ID NO:4:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:4:

GGTGGTGGGG GGGGGTGGGG TGGTGGTGGG GGTGTTGG 38

( 2 ) INFORMATION FOR SEQ ID NO:5:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:5:

GTGGTGGTGG TGTTGGTGGT GGTTTGGGGG GTGGGG 36

( 2 ) INFORMATION FOR SEQ ID NO:6:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:6:

GTGGTTGGTG GTGGTGTGTG GGTTTGGGGT GGGGGG 36

( 2 ) INFORMATION FOR SEQ ID NO:7:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 36
  ( D ) OTHER INFORMATION: /note="phosphorothioate backbone"

( x i ) SEQUENCE DESCRIPTION: SEQ ID NO:7:

GTGGTGGTGG TGTTGGTGGT GGTTTGGGGG GTGGGG 36

( 2 ) INFORMATION FOR SEQ ID NO:8:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 36
    ( D ) OTHER INFORMATION: /note="phosphorothioate backbone"

( x i ) SEQUENCE DESCRIPTION: SEQ ID NO:8:

GTGGTTGGTG GTGGTGTGTG GGTTTGGGGT GGGGGG                     36

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGTGGGGTGG TGGTGGTTGG GGGGGGGGGG T                          31

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GGTGGTTGGG GGGTGGGGGG G                                  21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGGTGGGGTG GTGGGTGGGG G                                  21

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGTGGGTGGT TTGTGTGGTT GGTGGGTTTT                            30

( 2 ) INFORMATION FOR SEQ ID NO:13:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GGGGGGGGGG TGTGGGGGGG GGTTGTGGTG G                                31

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GGTGGGTGGG TTGGGGGGTG GGTGGGG                                  27

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TGGGGTTTGG GTGGGGGGTT GGGTGGTTG                                29

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GGGTGGTGGT GTTGGTGTTG TGTG                                      24

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGTGGGGGGG TTGGTGTGTT TG                                          22

( 2 ) INFORMATION FOR SEQ ID NO:18:

( i ) SEQUENCE CHARACTERISTICS:
        ( A ) LENGTH: 26 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:18:

GTGTGGGGGG GTGGGGTGGG GTGGGT 26

( 2 ) INFORMATION FOR SEQ ID NO:19:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GGGTGGGTGG GTGGGTGGGT GGGTGG 26

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 26
        ( D ) OTHER INFORMATION: /note="Amine moity attached to 3'
           end"

( x i ) SEQUENCE DESCRIPTION: SEQ ID NO:20:

GTTGGGGGTT GTTGGTGGGG TGGTGG 26

( 2 ) INFORMATION FOR SEQ ID NO:21:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 45
        ( D ) OTHER INFORMATION: /note="Amine moity attached to 3'
           end"

( x i ) SEQUENCE DESCRIPTION: SEQ ID NO:21:

TGGTGGGTGT GTGGGGGGTG TTGGGGGTTG TTGGTGGGGT GGTGG 45

( 2 ) INFORMATION FOR SEQ ID NO:22:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 45
        ( D ) OTHER INFORMATION: /note="cholesterol moity attached to 3'end"

( x i ) SEQUENCE DESCRIPTION: SEQ ID NO:22:

TGGTGGGTGT GTGGGGGGTG TTGGGGGTTG TTGGTGGGGT GGTGG    45

( 2 ) INFORMATION FOR SEQ ID NO:23:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 45
        ( D ) OTHER INFORMATION: /note="cholesterol moity attached
            to 3'end"

( x i ) SEQUENCE DESCRIPTION: SEQ ID NO:23:

GTGGTGGGTG GGTGGGTGGT GGGTGGTGGT TGTGGGTGGG TGGTG    45

( 2 ) INFORMATION FOR SEQ ID NO:24:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 45
        ( D ) OTHER INFORMATION: /note="Amine moity attached to 3'
            end"

( x i ) SEQUENCE DESCRIPTION: SEQ ID NO:24:

GTGGTGGGTG GGTGGGTGGT GGGTGGTGGT TGTGGGTGGG TGGTG    45

( 2 ) INFORMATION FOR SEQ ID NO:25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 26
        ( D ) OTHER INFORMATION: /note="cholesterol moity attached
            to 3'end"

( x i ) SEQUENCE DESCRIPTION: SEQ ID NO:25:

GTTGGGGGTT GTTGGTGGGG TGGTGG    26

( 2 ) INFORMATION FOR SEQ ID NO:26:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: misc_feature
    ( B ) LOCATION: 45
    ( D ) OTHER INFORMATION: /note="Amine moiety attached to 3' end"

( x i ) SEQUENCE DESCRIPTION: SEQ ID NO:26:

GATCCATGTC AGTGACACTG CGTAGATCCG ATGATCCAGT CGATG　　45

( 2 ) INFORMATION FOR SEQ ID NO:27:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 26
    ( D ) OTHER INFORMATION: /note="phosphorothioate backbone and amine moiety attached to backbone"

( x i ) SEQUENCE DESCRIPTION: SEQ ID NO:27:

GTTGGGGGTT GTTGGTGGGG TGGTGG　　26

( 2 ) INFORMATION FOR SEQ ID NO:28:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:28:

GGTGGTGGGG TGGTTGTTGG GGGTTG　　26

( 2 ) INFORMATION FOR SEQ ID NO:29:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:29:

GGTGGTGGGG TGGTTGTTGG GGGTTGTTGG GGGTGTGTGG GTGGT　　45

( 2 ) INFORMATION FOR SEQ ID NO:30:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:30:

GGGTGGTTGG GTGGTTGG　　18

( 2 ) INFORMATION FOR SEQ ID NO:31:

( i ) SEQUENCE CHARACTERISTICS:

(A) LENGTH: 18 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: misc_feature
(B) LOCATION: 18
(D) OTHER INFORMATION: /note="Amine moity attached to 3' end"

(x i) SEQUENCE DESCRIPTION: SEQ ID NO:31:

GGGTGGGTGG GTGGGTGG                          18

(2) INFORMATION FOR SEQ ID NO:32:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: misc_feature
(B) LOCATION: 18
(D) OTHER INFORMATION: /note="Amine moity attached to 3' end and phosphothioate backbone"

(x i) SEQUENCE DESCRIPTION: SEQ ID NO:32:

GGGTGGGTGG GTGGGTGG                          18

(2) INFORMATION FOR SEQ ID NO:33:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: misc_feature
(B) LOCATION: 17
(D) OTHER INFORMATION: /note="Amine moity attached to 3' end"

(x i) SEQUENCE DESCRIPTION: SEQ ID NO:33:

GTGGTGGGTG GGTGGGT                           17

(2) INFORMATION FOR SEQ ID NO:34:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: misc_feature
(B) LOCATION: 27
(D) OTHER INFORMATION: /note="Amine moity attached to 3' end"

(x i) SEQUENCE DESCRIPTION: SEQ ID NO:34:

GTGGTGGGTG GGTGGGTGGT GGGTGGT                27

( 2 ) INFORMATION FOR SEQ ID NO:35:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 37
        ( D ) OTHER INFORMATION: /note="Amine moity attached to 3'
            end"

( x i ) SEQUENCE DESCRIPTION: SEQ ID NO:35:

GTGGTGGGTG GGTGGGTGGT GGGTGGTGGT TGTGGGT 37

( 2 ) INFORMATION FOR SEQ ID NO:36:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 16
        ( D ) OTHER INFORMATION: /note="Amine moity attached to 3'
            end"

( x i ) SEQUENCE DESCRIPTION: SEQ ID NO:36:

TTGTGGGTGG GTGGTG 16

( 2 ) INFORMATION FOR SEQ ID NO:37:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 29
        ( D ) OTHER INFORMATION: /note="Amine moity attached to 3'
            end"

( x i ) SEQUENCE DESCRIPTION: SEQ ID NO:37:

TGGTGGGTGG TGGTTGTGGG TGGGTGGTG 29

( 2 ) INFORMATION FOR SEQ ID NO:38:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 38
        ( D ) OTHER INFORMATION: /note="Amine moity attached to 3'
            end"

( x i ) SEQUENCE DESCRIPTION: SEQ ID NO:38:

GTGGGTGGGT GGTGGGTGGT GGTTGTGGGT GGGTGGTG                                    3 8

( 2 ) INFORMATION FOR SEQ ID NO:39:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 45
        ( D ) OTHER INFORMATION: /note="phosphorothioate backbone
            and amine moiety attached to 3'end"

( x i ) SEQUENCE DESCRIPTION: SEQ ID NO:39:

GTGGTGGGTG GGTGGGTGGT GGGTGGTGGT TGTGGGTGGG TGGTG                             4 5

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 18
        ( D ) OTHER INFORMATION: /note="Amine moity attached to 3'
            end"

( x i ) SEQUENCE DESCRIPTION: SEQ ID NO:40:

GATCCATGTC AGTGACAC                                                          1 8

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 18
        ( D ) OTHER INFORMATION: /note="Amine moity attached to 3'
            end and phosphorothioate backbone"

( x i ) SEQUENCE DESCRIPTION: SEQ ID NO:41:

GATCCATGTC AGTGACAC                                                          1 8

( 2 ) INFORMATION FOR SEQ ID NO:42:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature

-continued ( B ) LOCATION: 18
( D ) OTHER INFORMATION: /note="Amine moity attached to 3' end"

( x i ) SEQUENCE DESCRIPTION: SEQ ID NO:42:

CCCCCCCCC CCCCCCC                                                                                           18

( 2 ) INFORMATION FOR SEQ ID NO:43:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 18
( D ) OTHER INFORMATION: /note="Amine moity attached to 3' end and phosphorothioate backbone"

( x i ) SEQUENCE DESCRIPTION: SEQ ID NO:43:

CCCCCCCCC CCCCCCC                                                                                           18

( 2 ) INFORMATION FOR SEQ ID NO:44:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

TTCATTTGGG AAACCCTTGG AACCTGACTG ACTGGCCGTC GTTTTAC                                                         47

( 2 ) INFORMATION FOR SEQ ID NO:45:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:45:

GTAAAACGAC GGCCA                                                                                            15

ANTI-VIRAL GUANOSINE-RICH OLIGONUCLEOTIDES

The present invention is a continuation-in-part of U.S. patent application Ser. No. 08/053,027, filed Apr. 23, 1993 now abandoned.

BACKGROUND OF THE INVENTION

1. Field of the Invention

The present invention relates generally to the field of oligonucleotide chemistry and anti-viral pharmacotherapy. More specifically, the present invention relates to novel guanosine-rich oligonucleotides and their use as novel anti-viral agents.

2. Description of the Related Art

Previously, it was believed that "antisense" oligonucleotides inhibit viruses by interfering with protein translation via an RNA:DNA duplex structure. More recent research, however, indicates a variety of possible mechanisms by which oligonucleotides inhibit viral infections. For example, oligodeoxycytidine (poly SdC) inhibits HIV-1. Marshall et al., PNAS (1992) 89:6265–6269, discussed the potential mechanism (competitive inhibition) by which oligodeoxycytidine directly inhibits viral reverse transcriptase. Poly SdC also inhibited AMV reverse transcriptase and Pol I (Klenow fragment) and polymerase $\alpha$, $\beta$ and $\gamma$. Previously, Matsukura et al., PNAS (1987) 84:7706–7710, used a similar phosphorothioate derivative of oligodeoxycytidine to demonstrate inhibition of HIV-1 in culture. Marshall and Caruthers, Science (1993) 259:1564–1569, reported the use of diphosphorothioate oligonucleotides, e.g., antisense specific, random nucleotide combinations and oligodeoxycytidine against HIV-1. In all cases, the mechanism of action was attributed to a direct inhibition of HIV-1 reverse transcriptase. Other potential mechanisms of anti-viral action of oligonucleotides were postulated by Boiziau et al., PNAS (1992) 89:768–772, e.g., promotion of RNAse H activity and inhibition of reverse transcriptase initiating cDNA synthesis. In addition, Goa et al., Molecular Pharmacology (1992) 41:223–229 reported that phosphorothioate oligonucleotides inhibit human DNA polymerases and RNAse H, and the adsorption or penetration of the virus into cells. Iyer et al., Nucleic Acids Research (1990) 18:2855–2859 report that if a base was removed from an anti-sense polynucleotide forming an abasic site, the compound did not lose its activity which argues against the need for the formation of an RNA:DNA antisense mediated hybrid for anti-viral activity. Stein et al. have characterized the interaction of poly SdC with the V3 loop of HIV-1 gp120, and postulated that the specific interaction of poly SdC with the HIV-1 V3 loop may be a mechanism by which an oligonucleotide could inhibit HIV-1 in vivo.

It is known that synthetic oligonucleotides may be designed which are capable of binding to duplex DNA to form triplex DNA. See U.S. Pat. No. 5,176,996 Hogan & Kessler issued Jan. 5, 1993. This application describes a method for making synthetic guanosine-rich oligonucleotides which are targeted to specific sequences in duplex DNA and which form colinear triplexes by binding to the major groove of the DNA duplex.

SUMMARY OF THE INVENTION

In one embodiment of the present invention, there is provided a method of treating a pathophysiological state caused by a virus, comprising the step of administering a pharmacological dose of an oligonucleotide, said dose being sufficient to inhibit production of said virus, wherein said oligonucleotide contains a high percentage of guanosine bases.

In another embodiment of the present invention, there is provided a method of treating a pathophysiological state caused by a herpes simplex virus, comprising the step of administering a pharmacological dose of an oligonucleotide, said dose being sufficient to inhibit the replication of said virus, wherein said oligonucleotide contains a high percentage of guanosine bases.

In yet another embodiment of the present invention, there is provided a method of treating a pathophysiological state caused by human immunodeficiency viruses, comprising the step of administering a pharmacological dose of an oligonucleotide, said dose being sufficient to inhibit the replication of said virus, wherein said oligonucleotide contains a high percentage of guanosine bases.

In still yet another embodiment of the present invention, there is provided a method of treating a pathophysiological state caused by human papilloma virus, comprising the step of administering a pharmacological dose of an oligonucleotide, said dose being sufficient to inhibit the replication of said virus, wherein said oligonucleotide contains a high percentage of guanosine bases.

In still yet another embodiment of the present invention, there is provided a method of treating a pathophysiological state caused by human cytomegalovirus, comprising the step of administering a pharmacological dose of an oligonucleotide, said dose being sufficient to inhibit the replication of said virus, wherein said oligonucleotide contains a high percentage of guanosine bases.

In still yet another embodiment of the present invention, there is provided a method of treating a pathophysiological state caused by adenovirus, comprising the step of administering a pharmacological dose of a oligonucleotide, said dose being sufficient to inhibit the replication of said virus, wherein said oligonucleotide contains a high percentage of guanosine bases.

In still yet another embodiment of the present invention, there is provided a method of treating a pathophysiological state caused by hepatitis B virus, comprising the step of administering a pharmacological dose of a oligonucleotide, said dose being sufficient to inhibit the replication of said virus, wherein said oligonucleotide contains a high percentage of guanosine bases.

In still yet another embodiment of the present invention, there is provided a guanosine-rich oligonucleotide, wherein said oligonucleotides exhibits anti-viral activity.

In a further embodiment, the oligonucleotides of the present invention have partially or fully phosphorothioated backbones.

BRIEF DESCRIPTION OF THE DRAWINGS

FIGS. 1A–1D. FIG. 1A shows a 1973 base pair Hind III to Eco R1 sub fragment of the Friend Murine Leukemia Virus (FMLV) clone 57 genome. FIG. 1B shows a 172 base pair (Hind III to Stu I) fragment which is an expanded portion of the 1973 base pair fragment. Within this fragment is the purine rich target to which triple helix forming oligonucleotides are directed. FIG. 1C shows the entire Hind III/Eco R1 FMLV fragment cloned into the pT7-2 plasmid (United States Biochemical Corporation) yielding p275A. In this recombinant the Hind III site is 10 base pairs downstream of the T7 mRNA start site. The 5' portion of the triple helix target region is 63 base pairs downstream of the mRNA start and the Dde I site is 131 base pairs downstream of the mRNA start site. FIG. 1D shows the Hind III/Eco R1 FMLV fragment was cloned into pBS (Stratagene) yielding pBSFMLV. The Hind III site, triple helix target site and Dde I site are respectively 50, 103 and 171 base pairs downstream from the mRNA start site.

FIG. 5A shows that the reduction in full length transcripts directed by the T7 and T3 promoter when I100-51 (anti-parallel triple helix forming oligonucleotide; FMLV2ap) was added. Samples in which no oligonucleotide was added were counted and used as 100% transcription reference points. In all other reactions 4×10$^{-6}$M of G101-50 (4e-6) was added and where indicated G101-50 plus I100-51 at concentrations ranging from 2×10$^{-9}$ to 2×10$^{-6}$M (2e-9 to 2e-6). FIG. 5B shows the reduction in full length transcript by I100-01 (FMLV2p). T7 directed transcripts were treated as in FIG. A. G101-50 was added to each reaction except the control (no oligo) with or without various concentration of I100-01 or I100-11 (26% G-ctl). FIG. 5C shows the analysis of truncated (63 base pair) transcript.

DETAILED DESCRIPTION OF THE INVENTION

Figure 2:
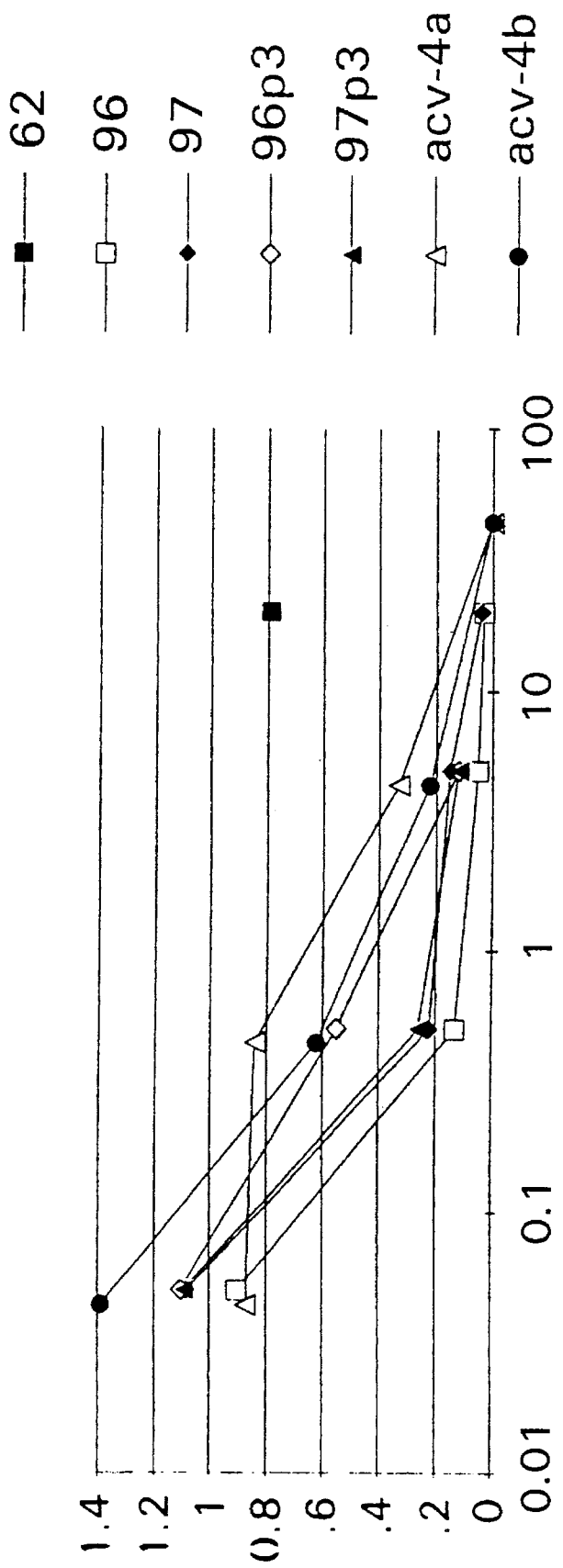
FIG. 2 shows that G-Rich phosphorothioated-oligonucleotides induced reduction in HSV-2 viral titer. VERO cells infected with HSV-2 were treated with various concentrations of the indicated drug. The results are plotted as percent virus yield relative to VERO cells infected with virus but not treated with drug (titer=1). The filled square (B106-62) represents a single concentration point (20 μM) for this oligonucleotide. B106-96 is the fully phosphorothioated version of B106-62. B106-97 is the fully phosphorothioated version of B106-71. ACV (4a and 4b) is acyclovir tested against two different stock concentrations of HSV-2 strain HG52. In two experiments, after virus infection and before reapplication of oligonucleotide, the cells were rinsed with a pH 3 buffer in order to remove all virus not yet internalized (96p3 and 97p3).

It is readily apparent to one skilled in the art that various substitutions and modifications may be made to the invention disclosed herein without departing from the scope and spirit of the invention.

The term "oligonucleotide" as used herein is defined as a molecule comprised of two or more deoxyribonucleotides or ribonucleotides, preferably more than ten. Its exact size will depend on many factors including the specificity and antiviral activity of the oligonucleotide for various viruses.

In referring to "bases" herein, the term includes both the deoxyribonucleic acids and ribonucleic acids. The following abbreviations are used. "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill would readily recognize that these bases may be modified or derivatized to optimize the methods of the present invention.

The term "inhibition" of viral replication is meant to include partial and total inhibition of viral replication as well as decreases in the rate of viral replication. The inhibitory dose or "therapeutic dose" of the compounds in the present invention may be determined by assessing the effects of the oligonucleotide on viral replication in tissue culture or viral growth in an animal. The amount of oligonucleotide administered in a therapeutic dose is dependent upon the age, weight, kind of concurrent treatment and nature of the viral condition being treated.

The term "pharmacological dose" as used herein refers to the dose of an oligonucleotide which causes a pharmacological effect when given to an animal or human. The pharmacological dose introduced into the animal or human to be treated, will provide a sufficient quantity of oligonucleotide to provide a specific effect, e.g., (1) inhibition of viral protein or enzymes, (2) inhibition of viral-specific replication, (3) preventing the target site from functioning or (4) damaging the duplex DNA at the specific site or (5) ablating the DNA at the site or (6) inhibiting the transcription/translation of the gene under the regulation of the site being bound or (7) internal inhibition of transcription or translation of the gene containing the sequence. One skilled in the art will readily recognize that the dose will be dependent upon a variety of parameters, including the age, sex, height and weight of the human or animal to be treated, the organism or gene location which is to be attacked and the location of the target sequence within the organism. Given any set of parameters, one skilled in the art will be able to readily determine the appropriate dose.

The term "pathophysiological state" as used herein refers to any abnormal, undesirable or life-threatening condition caused directly or indirectly by a virus.

The present invention provides a method of treating a pathophysiological state caused by a virus, comprising the step of administering a pharmacological dose of an oligonucleotide, said dose being sufficient to inhibit the replication of said virus, wherein said oligonucleotide contains a high percentage of guanosine bases. Generally, this method of treating a virus-induced pathophysiological state may be useful against any virus. More preferably, the methods of the present invention may be useful in treating pathophysiological states caused by viruses such as herpes simplex virus, human papilloma virus, Epstein Barr virus, human immunodeficiency virus, adenovirus, respiratory syncytial virus, hepatitis B virus, human cytomegalovirus and HTLV I and II.

Generally, the oligonucleotides of the present invention contain a percentage of guanosine bases high enough to ensure anti-viral efficacy. Thus, the oligonucleotides of the present invention may have any percentage of guanosine bases provided that the oligonucleotide exhibits anti-viral activity. Preferably, the oligonucleotides of the present invention contain at least about 50% guanosine bases.

Generally, the oligonucleotides of the present invention may be capped at either the 3' or the 5' terminus with a modifier. Preferably, the modifier is selected from the group consisting of polyamine or similar compounds that confer a net positive charge to the end of the molecule, poly-L-lysine or other similar compounds that enhance uptake of the oligonucleotide, cholesterol or similar lipophilic compounds that enhance uptake of the oligonucleotide and propylamine or similar amine groups that enhance stability of the molecule.

The phosphodiester linkage of the oligonucleotides of the present invention may be modified to improve the stability or increase the anti-viral activity. For example, the phosphodiester backbone of the oligonucleotide may be modified to a phosphorothioate linkage. Other such modifications to the oligonucleotide backbone will be obvious to those having ordinary skill in this art.

The present invention also provides specific methods of treating viral states. For example, the present invention provides a method of treating a pathophysiological state caused by a herpes simplex virus, comprising the step of administering a pharmacological dose of an oligonucleotide, said dose being sufficient to inhibit the replication of said virus, wherein said oligonucleotide contains a high percentage of guanosine bases. Also provided in the instant application is a method of treating a pathophysiological state caused by human immunodeficiency virus, comprising the step of administering a pharmacological dose of an oligonucleotide, said dose being sufficient to inhibit the replication of said virus, wherein said oligonucleotide contains a high percentage of guanosine bases. The present invention also provides a method of treating a pathophysiological state caused by human papilloma virus, comprising the step of administering a pharmacological dose of an oligonucleotide, said dose being sufficient to inhibit the replication of said virus, wherein said oligonucleotide contains a high percentage of guanosine bases. In addition, the present invention provides a method of treating a pathophysiological state caused by human cytomegalovirus, comprising the step of administering a pharmacological dose of an oligonucleotide, said dose being sufficient to inhibit the replication of said virus, wherein said oligonucleotide contains a high percentage of guanosine bases. The present invention also provides a method of treating a pathophysiological state caused by hepatitis B virus, comprising the step of administering a pharmacological dose of an oligonucleotide, said dose being sufficient to inhibit the replication of said virus, wherein said oligonucleotide contains a high percentage of guanosine bases.

This invention discloses a novel anti-viral technology. The total number of antiviral mechanisms by which oligonucleotides, and especially G-rich oligonucleotides, work is not known. However in the different virus culture systems listed above, G-rich oligonucleotides were able to significantly reduce virus production in each. Prior to this invention, investigators tried to establish anti-viral mechanism based on anti-sense technology, and yet the present invention shows that oligonucleotide exhibition of anti-viral activity is not via inhibition of translation events.

The present invention demonstrates poly and/or oligonucleotides inhibit growth of HIV-1, HCMV, HSV2, FMLV and other viruses if the molecule contains a high percentage of ribo- or deoxyriboguanosine. The rest of the molecule is composed of thymine, cytosine, xanthosine or adenine nucleotides (ribo or deoxyribo) or their derivatives. The 5' and 3' termini of the oligonucleotide can have any attachment which may enhance stability, uptake into cells (and cell nuclei) or anti-viral activity. The backbone which connects the nucleotides can be the standard phosphodiester linkage or any modification of this linkage which may improve stability of the molecule or anti-viral activity of the molecule (such as a phosphorothioate linkage).

Structural formulas for several different G-rich oligonucleotides disclosed in the instant invention are listed below in Table 1. All oligonucleotides listed here have a propylamine group attached to their 3' end. This amine group confers stability against nuclease digestion to these oligonucleotides.

TABLE 1

| SEQ ID NO 5(B106-62) | 5'-gtggtggtggtgttggtggtggtttgggggtgggg-3' |
|---|---|
| SEQ ID NO 6(B106-71) | 5'-gtggttggtggtggtgtgtgggtttggggtggggg-3' |

TABLE 1-continued

| | |
|---|---|
| SEQ ID NO 21(I100-01) | 5'-tggtgggtgtgtgggggtgttgggggttgttggtggggtggtgg-3' |
| SEQ ID NO 24(I100-07) | 5'-gtggtgggtgggtgggtggtgggtggtggttgtgggtgggtggtg-3' |
| SEQ ID NO 28(I100-50) | 5'-ggtggtggggtggttgttggggttg-3' |
| SEQ ID NO 29(I100-51) | 5'-ggtggtggggtggttgttggggttgttgggggtgtgtgggtggt-3' |
| SEQ ID NO 26(I100-11) | 5'-gatccatgtcagtgacactgcgtagatccgatgatccagtcgatg-3' |
| SEQ ID NO 12(G101-50) | 5'-ggtgggtggtttgtgtggttggtgggtttt-3' |
| SEQ ID NO 13(G105-50) | 5'-ggggggggggtgtgggggggggttgtggtgg-3' |
| SEQ ID NO 14(G106-50) | 5'-ggtgggtggggttgggggggtgggtgggg-3' |
| SEQ ID NO 15(G109-50) | 5'-tggggtttgggtggggggttgggtggttg-3' |
| SEQ ID NO 16(G110-50) | 5'-gggtggtggtgttggtgttgtgtg-3' |
| SEQ ID NO 17(G113-50) | 5'-ggtgggggggggttggtgtgtttg-3' |
| SEQ ID NO 1(A100-00) | 5'-tggggtggggtggggtgggggggtgtgggtgtggggtg-3' |
| SEQ ID NO 2(A100-50) | 3'-tggggtggggtggggtgggggggtgtgggtgtggggtg-5' |
| SEQ ID NO 4(A101-00) | 5'-ggtgggtggggggggtgggggtggtggtgggggtgttgg-3' |
| SEQ ID NO 18(HIV26ap) | 5'-gtgtgggggggtggggtggggtgggt-3' |
| SEQ ID NO 19(HIV26ctl) | 5'-gggtgggtgggtgggtgggtgggtgg-3' |
| SEQ ID NO 9(B107-51) | 5'-ggtggggtggtggtggttggggggggggggt-3' |
| SEQ ID NO 10(B133-55) | 5'-ggtggttgggggggtgggggggg-3' |
| SEQ ID NO 11(B133-55) | 5'-gggtggggtggtgggtggggg-3' |
| SEQ ID NO 20(I100-00) | 5'-gttgggggttgttggtggggtggtgg-3' |
| SEQ ID NO 27(I100-12) | 5'-gttgggggttgttggtggggtggtgg-3' (PT) |
| SEQ ID NO 22(I100-05) | 5'-tggtgggtgtgtgggggtgttgggggttgttggtggggtggtgg-CHOL |
| SEQ ID NO 23(I100-06) | 5'-gtggtgggtgggtgggtggtgggtggtggttgtgggtgggtggtg-CHOL |
| SEQ ID NO 25(I100-08) | 5'-gttgggggttgttggtggggtggtgg-CHOL |
| SEQ ID NO 3 | 5'-gggtgggtgggtgggtgg-3' |
| SEQ ID NO 30 | 5'-gggtggttgggtggttgg-3' |
| SEQ ID NO 31(1173) | 5'-gggtgggtgggtgggtgg-3' |
| SEQ ID NO 32(1174, PT) | 5'-gggtgggtgggtgggtgg-3' |
| SEQ ID NO 33(I100-15) | 5'-gtggtgggtgggtgggt-3' |
| SEQ ID NO 34(I100-16) | 5'-gtggtgggtgggtgggtggtgggtggt-3' |
| SEQ ID NO 35(I100-17) | 5'-gtggtgggtgggtgggtggtgggtggtggttgtgggt-3' |
| SEQ ID NO 36(I100-18) | 5'-ttgtgggtgggtggtg-3' |
| SEQ ID NO 37(I100-19) | 5'-tggtgggtggtggttgtgggtgggtggtg-3' |
| SEQ ID NO 38(I100-20) | 5'-gtggggtgggtggtgggtggtggttgtgggtgggtggtg-3' |
| SEQ ID NO 39(I100-21, PT) | 5'-gtggtgggtgggtgggtggtgggtggtggttgtgggtgggtggtg-3' |
| SEQ ID NO 40(1231) | 5'-gatccatgtcagtgacac-3' |
| SEQ ID NO 41(1232, PT) | 5'-gatccatgtcagtgacac-3' |
| SEQ ID NO 42(1229) | 5'-cccccccccccccccccc-3' |
| SEQ ID NO 43(1230, PT) | 5'-cccccccccccccccccc-3' |
| SEQ ID NO 44(1198) | 5'-ttcatttgggaaaccccttggaacctgactgactggccgtcgttttac-3' |
| SEQ ID NO 45(1200) | 5'-gtaaaacgacggcca-3' |

The present invention also provides novel guanosine-rich oligonucleotides having anti-viral activity.

The following examples are offered by way of illustration and are not intended to limit the invention in any manner.

EXAMPLE 1

HSV-2 Culture Assay

In viral yield reduction assays, Vero cells ($4 \times 10^4$ cells/tissue culture well) were incubated with oligonucleotide(s) for 14 hours before the oligonucleotide was removed and virus (HSV-2 strain HG52) added to the cells at a multiplicity of infection (m.o.i.) of 0.1 to 1.0 ($4 \times 10^3$ to $4 \times 10^4$ PFU). The infection was allowed to proceed for 10 minutes after which the cells are washed and fresh media, containing the same oligonucleotide is added for an additional 14 hours. Then the cells are subjected to a freeze/thaw lysis after which the released virus is titered.

EXAMPLE 2

HIV-1 Culture Assay

The SUP T1 T lymphoma cell line was infected with HIV-1 strain DV at a multiplicity of infection (m.o.i.) of 0.1 for one hour at 37° C. After the infection, free virus was washed off and the newly infected cells were plated ($5 \times 10^4$ cells) in quadruplicate in 96 well plates that had been prepared with various dilutions of oligonucleotide. The final concentration of drug varied between 0.1 and 20 uM. After 3 days of incubation at 37° C., the plates were scored for the presence of multinucleated giant cells (syncytia).

In assays designed to inhibit syncytia formation, a number of oligonucleotides exhibited anti-HIV-1 activity. The oligonucleotides and their ED50 are listed in Table 2. I100-05 is the same as I100-01 with a cholesterol group attached to the 3' end via a triglycyl-linker. I100-08 is the same as I100-00 with a cholesterol group attached to the 3' end via a triglycyl-linker. I100-07 was designed as a sequence isomer to I100-01 and I100-06 is the cholesterol derivative of I100-07. A100-00 is the parallel configuration of the anti-HIV-1 oligonucleotide (HIV38p). I100-07, originally designed as a control for I100-01 to be used in anti-FMLV experiments, was the most efficacious oligonucleotide tested against HIV-1.

Figure 3:
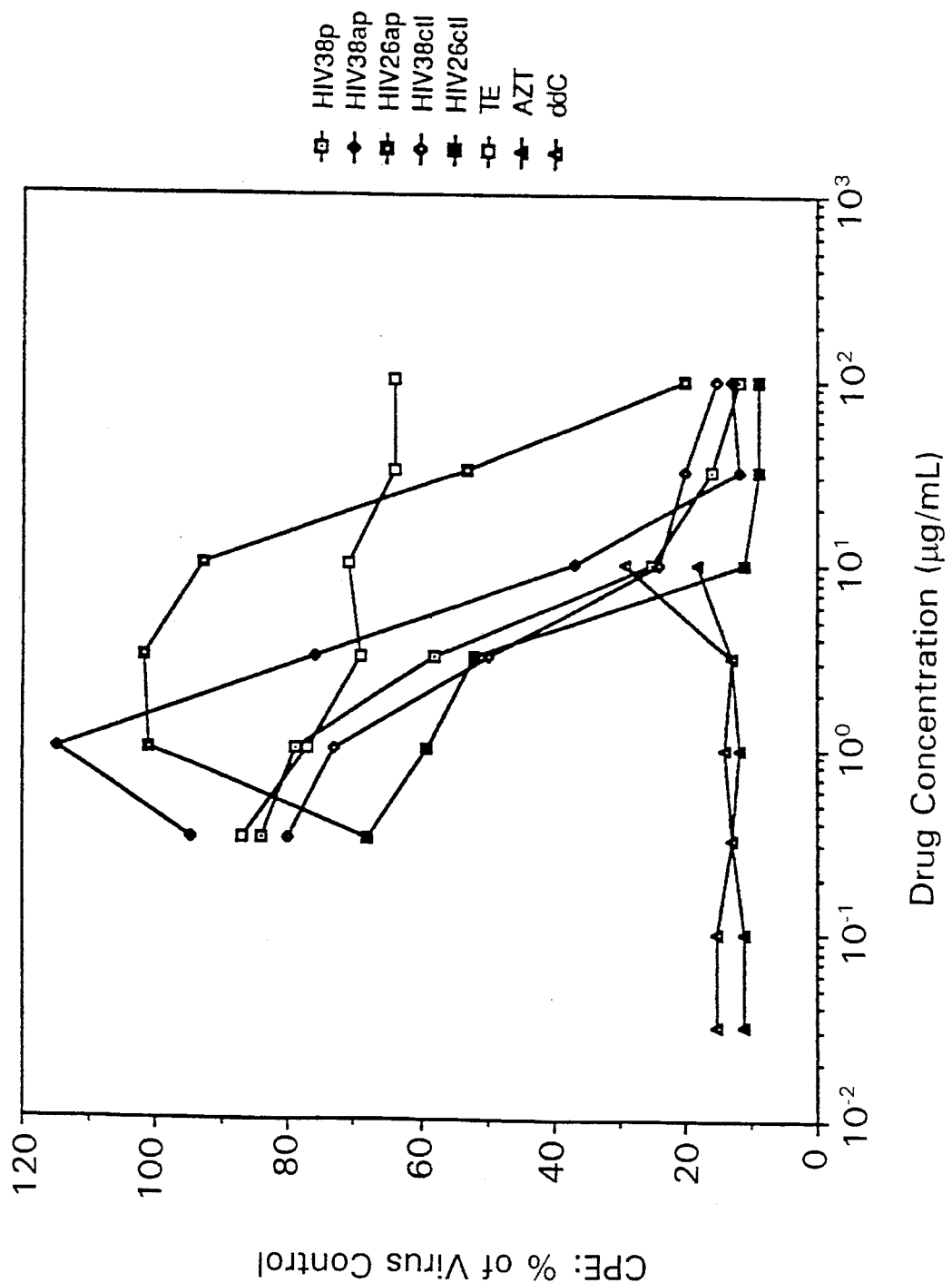
FIG. 3 shows that the MT-2 cells infected with 0.01 m.o.i. of HIV-1 were treated with various concentrations of oligonucleotide or AZT or ddC. The data represents the number of viable cells remaining in the culture dish, i.e., not undergoing virus induced cytopathic effects (CPE). In this graph, 100% is the level of CPE occurring in cultures infected with virus but not treated with any drug.

In other experiments, the HIV-1 strain LAV was used to infect MT-2 cells at an m.o.i of 0.01. After 7 days, these cells were scored for cytopathic effects (CPE). In anti-HIV-1 assays in which MT-2 cells were infected at an m.o.i. of 0.01, several G-Rich oligonucleotides were able to inhibit viral-induced cytopathic effects with effective dose 50's (ED50s) in the 0.5–1.0 uM range (FIG. 3). The oligonucleotides shown in FIG. 3 were effective in the 0.5 to 1.0 uM range, including A100-00 (HIV38p) and A100-50 (HIV38ap), A101-00 (HIV38ctl), HIV-26ctl. The oligonucleotide HIV-26ap exhibited less efficacy in this assay with an ED50 in the 5 to 10 uM range. In FIG. 3, TE represents buffer alone, i.e., no drug, while AZT and ddC are control drugs.

TABLE 2

ED$_{50}$ for oligonucleotides in an anti-HIV-1 syncytia formation assay.

| G-Rich oligonucleotide | ED50 |
| --- | --- |
| I100-00 | 3.75 μM |
| I100-01 | 4.50 μM |
| I100-05 | 3.25 μM |
| I100-08 | 3.25 μM |
| I100-06 | 0.70 μM |
| I100-07 | 0.25 μM |
| A100-00 | 3.25 μM |

EXAMPLE 3

FMLV Culture Assay

Friend Murine Leukemia Virus (FMLV) was grown in a chronically infected murine fibroblast cell line (pLRB215) or can be propagated in an acute assay system by infection of NIH3T3 cells. When the chronically infected cell line was used, pLRB215 cells were split (1×10$^5$) into 24 well culture dishes and incubated 16 to 20 hours at 37° C. The media was then removed and replaced with media containing various concentrations of oligonucleotide. After 1, 3 or 5 days, culture media was assayed for the presence of the viral reverse transcriptase enzyme.

In acute assays, NIH3T3 cells were split (1×10$^4$) into 96 well dishes and allowed to incubate for 16–20 hours. After incubation, culture media was removed and concentrated virus stock (10 ul) was added to each well in 100 ul of completed media containing 2 ug/ml polybrene. The virus infection was allowed to proceed for 18 hours at which time the virus containing media was removed and complete media containing various concentrations of oligonucleotide was added. After 4 to 7 days, the culture media was assayed for the presence of viral reverse transcriptase.

EXAMPLE 4

HCMV Culture Assay

Human cytomegalovirus was cultured in the human diploid lung fibroblast cell line MRC-5. These cells were split and placed into 24 well culture dishes and preincubated for 24 hours with various concentrations of oligonucleotide (0.5 to 20 uM) in complete media. The oligonucleotide was then washed off and virus was added to the cells (approximately 0.1 m.o.i.) for 2 hours at 37° C. The virus was then removed and complete media containing the same concentration of oligonucleotide was added. Cells were then placed at 37° C. for 10–12 days at which time virus in the culture media was titered using a standard agar overlay procedure.

EXAMPLE 5

Bacterial T3 and T7 Assays

In this assay system, a 2 kb fragment (HindIII to Ecor R1) of the FMLV virus (clone 57) was molecularly cloned between the Hind III/Eco R1 sites 10 bp downstream of the bacterial T7 promoter (p275A) or 50 bp downstream of the bacterial T3 promoter (pBSFMLV2). A schematic representation of these two recombinant plasmids can be seen in FIG. 1. Isolated recombinant DNA was then digested with Dde I. Oligonucleotides were incubated then with the digested DNA and then subjected to in-vitro transcription using either the T7 or T3 bacterial enzymes.

EXAMPLE 6

Reverse Transcriptase Assay

In this assay, reverse transcriptase (either MMLV which is commercially available or FMLV from pLRB215 culture media) was incubated with various concentrations of oligonucleotide and then assayed using the enzyme linked oligonucleotide sorbent assay (ELOSA), the ELOSA kit is commercially available from New England Nuclear.

EXAMPLE 7

Eukaryotic In Vitro Transcription

In this assay, a recombinant plasmid containing the HSV-1 IE175 promoter fused to the bacterial chloramphenicol acetyltransferase gene (CAT) was linearized and used as a template for run off transcription studies. The commercially available HeLa cell nuclear extracts or prepared nuclear extracts of HSV-2 infected VERO cell were used.

EXAMPLE 8

Inhibition of HSV-2 Activity

The oligonucleotide B106-62 was originally designed to form a triple helix structure with a portion of the promoter region of the major immediate early protein of HSV-2 (IE175). The phosphorothioate derivatives of these two oligonucleotides were synthesized and tested for anti-viral activity against HSV-2. FIG. 2 shows that the B106-62 oligonucleotide at 20 μM was able to reduce viral titers by approximately 20% whereas the phosphorothioate version (B106-96) reduced virus by 50% in the submicromolar concentration range. The control oligonucleotide (B106-97), the phosphorothioate backbone derivative of B106-71, was also able to inhibit virus at the same levels as B106-96. Even when an extensive washing procedure at a pH of 3 was employed to remove excess virus not internalized during the infection, incubation with both B106-96 and B106-97 were able to significantly reduce virus yield. Thus, the mechanism of anti-viral activity was not just blocking adsorption of HSV-2 virions to cells.

FIG. 2 also shows the results of acyclovir in the same molar range as the oligonucleotides. Acyclovir was tested against two different stocks of HSV-2 strain HG52, as illustrated in FIGS. 4a and 4b.

EXAMPLE 9

Oligonucleotide Synthesis

The 47-mer DNA template oligonucleotide used was SEQ.ID. NO. 44 (1198) and the 15-mer primer sequence was SEQ.ID. NO. 45 (1200). All oligonucleotides used in these examples were synthesized on a DNA synthesizer (Applied Biosystems, Inc., model 380B or 394), using standard phosphoramidite methods. All oligonucleotides were synthesized with an amino modified 3'-terminal, which results in the covalent attachment of a propanolamine group to the 3'-hydroxyl group or with a cholesterol moiety attached to the 3'-terminal via a triglycyl-linker. Oligonucleotides used in this example were capped at their 3'-terminal with either a propylamine or a cholesterol moiety to reduce degradation by cellular exonucleases. Phosphorothioate containing oligonucleotides were prepared using the sulfurizing agent TETD. The 3'-cholesteryl modified oligonucleotides were prepared and purified as described by Vu et al. (in *Second International Symposium on Nucleic Acids Chemistry*, Sapporo, Japan, 1993).

Figure 6:
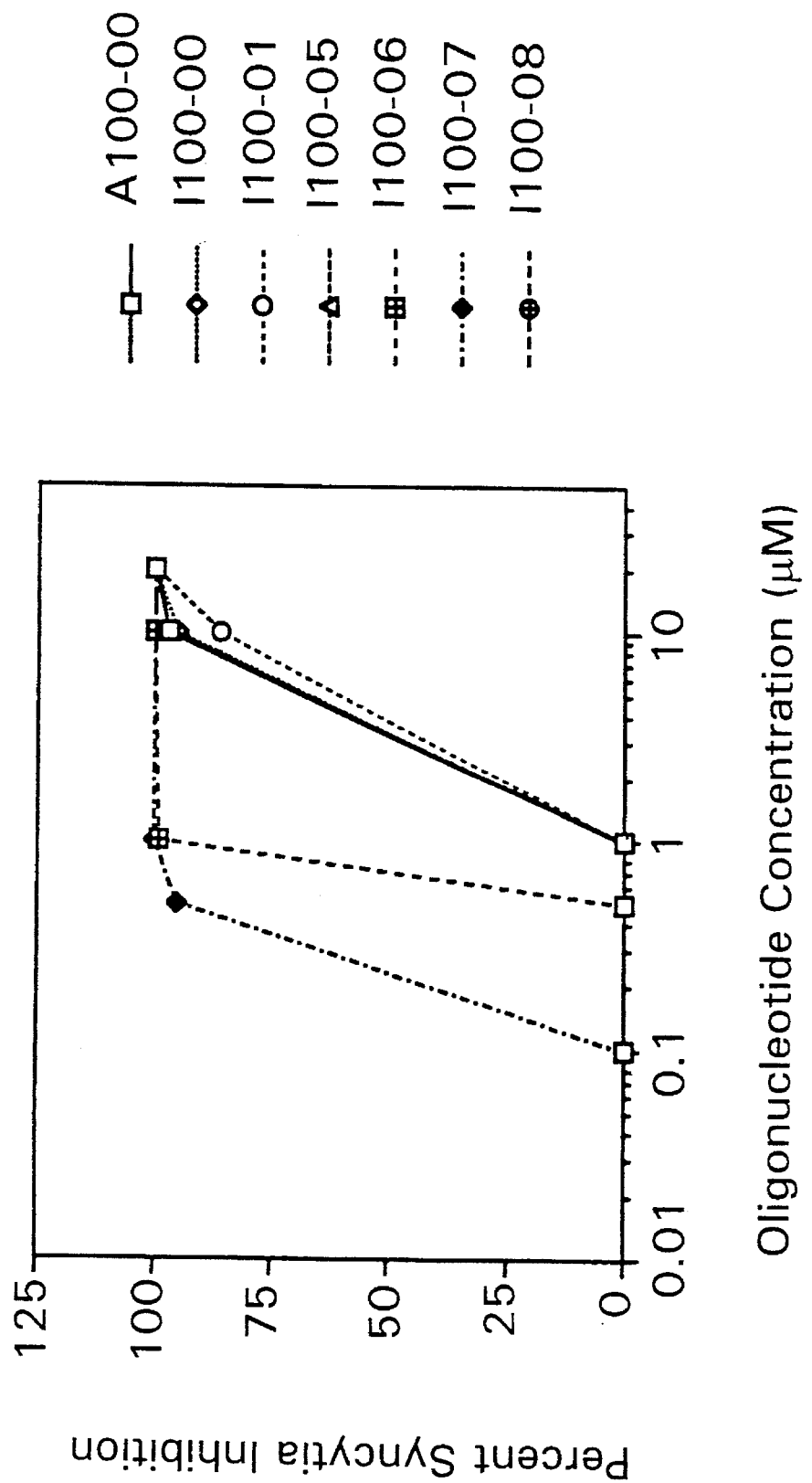
FIG. 6 shows inhibition of HIV-1 induced syncytia formation four days post-infection. SUP T1 cells were infected with HIV-1$_{DV}$ for four hours and then treated with various concentrations of oligonucleotides. Four days post-infection cells were scored for syncytia formation. All assays were performed in quadruplicate and the average values used to plot this graph. The legend to the right of the graph indicates the symbol used for each oligonucleotide tested.

Oligonucleotides with either full length phosphodiester (PD) or full length phosphorothioate (PT) backbones were stable in the culture media for 4 days while oligonucleotides consisting of a more random composition of nucleotides were rapidly degraded. This indicates that the 3'-modified G-rich oligonucleotides with PD backbones were stable against both endonuclease and exonuclease digestion over a defined four day incubation in culture. The concentration of oligonucleotide needed to reduce cell proliferation by 50% ($TC_{50}$) of selected compounds, based on the dye metabolism assay was approximately 40 to 50 µM for oligonucleotides with PD backbones and 15 to 25 µM for those compounds containing a PT backbone. The $TC_{50}$ for selected oligonucleotides are presented in Table 3.

assay system (FIG. 6, Table 4). Table 4 shows that I100-07 was approximately 10 fold more effective at reducing syncytia formation than the other sequence motifs listed.

TABLE 4

Inhibition of HIV-1 induced syncytia formation in SUP T1 cells

| Oligonucleotide | length | back-bone[a] | 3' end | mod.ED50 (syncytia) |
|---|---|---|---|---|
| A100-00 | 38 mer | PD | propylamine | 3.25 µM |
| I100-00 | 26 mer | PD | propylamine | 3.25 µM |
| I100-08 | 26 mer | PD | cholesterol | 3.25 µM |
| I100-01 | 45 mer | PD | propylamine | 4.50 µM |
| I100-05 | 45 mer | PD | cholesterol | 3.25 µM |
| I100-07 | 45 mer | PD | propylamine | 0.25 µM |
| I100-06 | 45 mer | PD | cholesterol | 0.75 µM |

[a]The backbone linkages were either phosphodiester (PD) or phosphorothioate (PT).

TABLE 3

Guanosine/thymidine and control oligonucleotide sequences

| Oligo[a] | Length | 3'-Modification[b] | Sequence | $TC_{50}$[c] |
|---|---|---|---|---|
| I100-07 | 45 mer | amine | \~5'-gtggtgggtgggtgggtggtgggtggtggttgtgggtgggtggtg-3' | >50 µM |
| I100-06 | 45 mer | cholesterol | 5'-gtggtgggtgggtgggtggtgggtggtggttgtgggtgggtggtg-3'\~ | |
| I100-00 | 26 mer | amine | 5'-                           gttggggttgttggtgggtggtgg-3'\~ | 37 µM |
| I100-08 | 26 mer | cholesterol | 5'-                           gttggggttgttggtgggtggtgg-3' | |
| I100-12 | 26 mer | amine (PT) | 5'-                           gttggggttgttggtgggtggtgg-3' | 18 µM |
| I100-01 | 45 mer | amine | 5'-tggtgggtgtgtgggggggtgttgggggttgttggtgggtggtgg-3' | |
| I100-05 | 45 mer | cholesterol | \~5'-tggtgggtgtgtgggggggtgttgggggttgttggtgggtggtgg-3' | |
| A100-00 | 38 mer | amine | \~5'-tgggtggggtggggtgggggggtgtggggtgtggggtg     -3'\~ | |
| 1173 | 18 mer | amine | \~5'-gggtgggtgggtgggtgg     -3'\~ | |
| I100-11 | 45 mer | amine | \~5'-gatccatgtcagtgacactgcgtagatccgatgatccagtcgatg-3' | 46.5 µM |
| 1231 | 18 mer | amine | 5'-gatccatgtcagtgacac     -3'\~ | |
| 1229 | 18 mer | amine | \~5'-cccccccccccccccccc     -3'\~ | |

[a]All oligonucleotides listed were synthesized with phosphodiester backbones except I100-12 which had phosphorothioate (PT) linkages.
[b]The capping group at the 3'-end of the oligonucleotide was either a propylamine or cholesterol moiety.
[c]Median inhibitory (toxic) concentration in tissue culture.

EXAMPLE 10

Inhibition of HIV-1 Production in an Acute Assay System

One stage in the progression of acquired immune deficiency syndrome is the loss of CD4+ lymphocytes through HIV-1 induced syncytia formation. SUP T1 cells were infected with HIV-1$_{DV}$, treated with various concentrations of oligonucleotides and then scored for syncytia formation 4 days post-infection. Three different sequence motifs, which were 38 (A100-00) or 45 (I100-01 and I100-07) nucleotides in length, indicated that the oligonucleotides were capable of inhibiting HIV-1 induced syncytia formation (FIG. 6). A shorter version of I100-01 (I100-00, 26 mer) was comparable to the inhibitory effect obtained for I100-01 (FIG. 6). The median effective dose ($ED_{50}$) for each oligonucleotide is presented in Table 4. Replacement of the 3'-propylamine group on the oligonucleotides with a triglycyl-linked cholesterol moiety (I100-05, I100-06 and I100-08) did not enhance the anti-viral activity of these compounds in this Analysis of six I100-07 PD size variants revealed that I100-15 (17 mer) was just as effective at reducing syncytia formation as I100-07 (45 mer) (see Table 5). In addition, a variation in the activity of the oligonucleotides was observed, dependent on which end of I100-07 the deletions were started from (Table 5). This is of interest since the first 14 nucleotides from either end of I100-07 are palindromic. The ($ED_{50}$) values of I100-21 and I100-17, indicating the ability to reduce HIV-1 p24 levels produced in the culture medium, were roughly equivalent to the oligonucleotide concentrations needed to reduce syncytia formation by the same amount (Table 5). The phosphorothioate containing oligonucleotides (I100-12 and I100-21) had the ability to inhibit HIV-1 syncytia formation and production of HIV-1 p24 in the SUP T1 acute assay system. This indicated that the presence of sulfur molecules in the backbone greatly enhanced the anti-viral activity of I100-00 (I100-12) and had a smaller enhancing effect on I100-07 (I100-21) (Table 5).

TABLE 5

Inhibition of HIV-1 induced syncytia formation and HIV-1 p24 production by G-rich oligonucleotides

| | | | | ED$_{50}$ (μM)[b] | |
|---|---|---|---|---|---|
| Oligo | Length | Modifications[a] | Sequence | Syncytia | p24 |
| I100-07 | 45 mer | PD | \~5'-gtggtgggtgggtgggtggtgggtggtggttgtgggtgggtggtg-3' | 0.25 | 0.55 |
| I100-21 | 45 mer | PT | 5'-gtggtgggtgggtgggtggtgggtggtggttgtgggtgggtggtg-3'\~ | 0.225 | <0.20 |
| I100-20 | 38 mer | PD | 5'-      gtgggtgggtggtgggtggtggttgtgggtgggtggtg-3' | 1.00 | 1.00 |
| I100-19 | 29 mer | PD | 5'-      tggtgggtggtggttgtgggtgggtggtg-3' | 3.75 | 2.00 |
| I100-18 | 16 mer | PD | 5'-      ttgtgggtgggtggtg-3' | 3.75 | 3.00 |
| I100-17 | 37 mer | PD | 5'-gtggtgggtgggtgggtggtgggtggtggttgtgggt   -3' | 0.30 | 0.20 |
| I100-16 | 27 mer | PD | 5'-gtggtgggtgggtgggtggtgggtggt   -3' | 0.25 | <0.20 |
| I100-15 | 17 mer | PD | \~5'-gtggtgggtgggtgggt   -3'\~ | 0.125 | <0.20 |
| I100-00 | 26 mer | PD | \~5'-gttggggttgttggtggggtggtgg   -3' | 3.75 | ND[c] |
| I100-12 | 26 MER | PT | 5'-gttggggttgttggtggggtggtgg   -3'\~ | 0.225 | <0.20 |

[a]The backbone modifications are denoted as PD for phosphodiester and PT for phosphorothioate. All oligonucleotides contained a 3' propylamine group.
[b]When AZT was used in these experiments and ED$_{50}$ of <0.04 μM ws obtained for both inhibition of syncytia and p24 antigen.
[c]Value not determined (ND).

Figure 7:
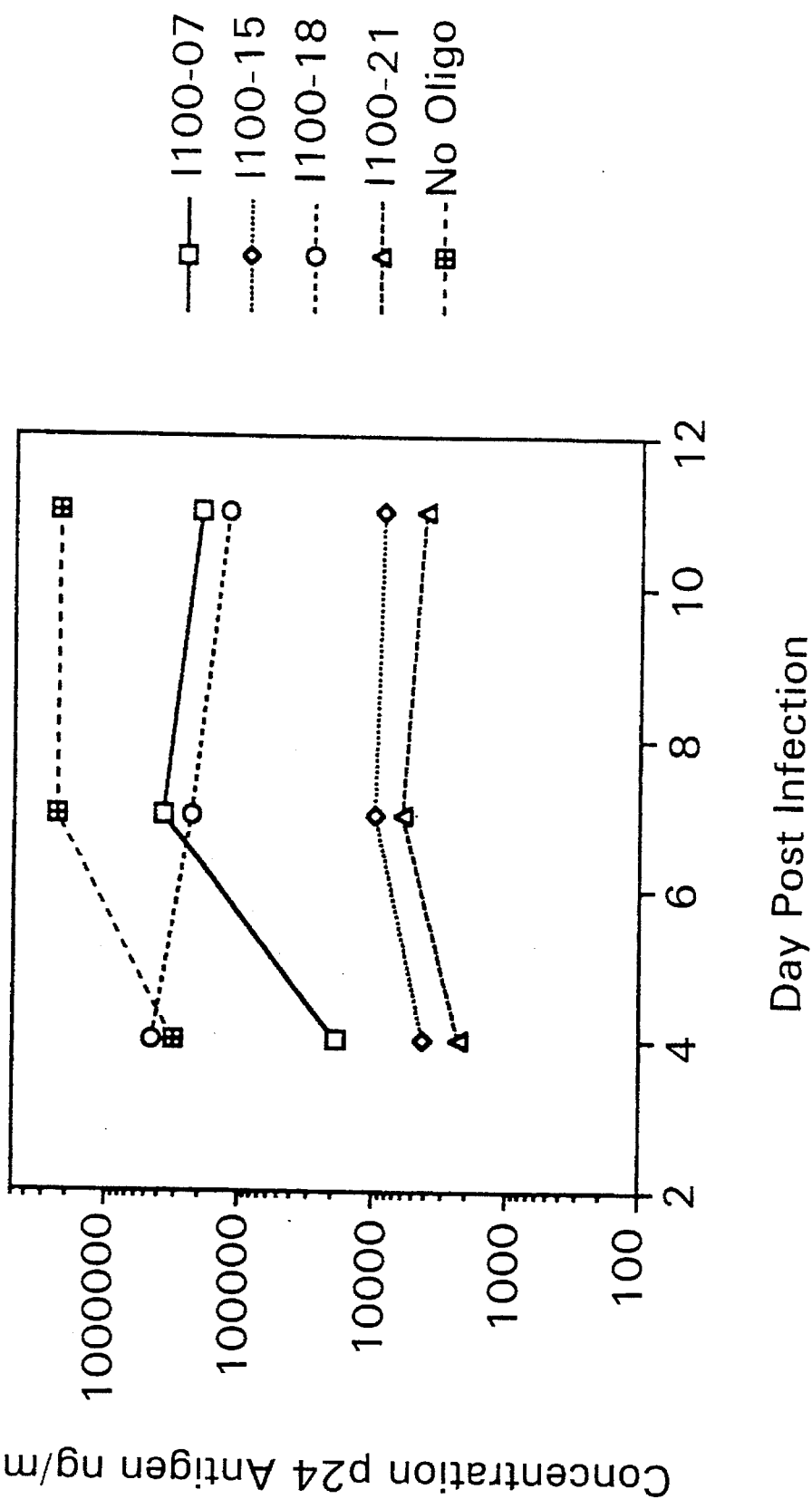
FIG. 7 shows continued suppression of HIV-1 p24 production seven days post removal of oligonucleotide. Four days post-infection with HIV-1$_{DV}$, the media from infected cells treated with oligonucleotides (2.5 μM) was removed and replaced with fresh media without oligonucleotide. The presence of viral p24 antigen was then assayed 7 and 11-days post infection. All samples were assayed in quadruplicate and the average values used to plot this graph. The legend to the right of the graph indicates the symbol used for each oligonucleotide tested.

The duration of the viral suppression was assayed by replacing culture media of HIV-1 infected cells, treated with 2.5 uM of various oligonucleotides, on day 4 post-viral infection with complete media without added oligonucleotides. The production of viral p24 antigen was then monitored on day 7 and day 11 post-infection. The short size variants of I100-07 (I100-15 and I100-16) as well as the PT version (I100-21) were capable of totally suppressing HIV-1 p24 production for at least 7 days after removal of the drug from the culture media (FIG. 7). The quantitation of p24 production relative to untreated HIV-1 infected SUPT1 cells is presented in Table 6. The presence of sulfur molecules in the backbone of oligonucleotide I100-07 (I100-21) had a more marked effect on the reduction of virus for the seven days after removal of compound from the culture media than was observed at the four day post-infection assay point (Table 5).

TABLE 6

Detection of HIV-1 p24 antigen in the culture media of GTO treated SUP T1 cells

| | Percent p24[a] | | |
|---|---|---|---|
| Oligonucleotide (2.5 mM) | Day 4[b] | Day 7 | Day 11 |
| Control SUP T1 cells[c] | 100.0 | 100.0 | 100.0 |
| I100-07 | 6.0 | 15.9 | 8.6 |
| I100-15 | 0.0 | 0.0 | 0.0 |
| I100-16 | 0.0 | 0.0 | 0.0 |
| I100-18 | 144.5 | 9.7 | 5.3 |
| I100-19 | 208.0 | 21.8 | 15.0 |
| I100-21 (PT)[d] | 0.0 | 0.0 | 0.0 |
| I100-12 (PT)[d] | 0.0 | 0.0 | 0.0 |

[a]Level of detectable p24 in culture medium relative to control (infected but untreated) SUP T1 cells after subraction of background values.
[b]Day 4 post-infection culture media was replaced with fresh media without oligonucleotide.
[c]SUP T1 cells infected with HIV-1 but not treated with oligonucleotides or AZT were used as positive control cells in this experiment.
[d]I100-21 and I100-12 contain phosphorothioate backbone linkages (PT).

Figure 8:
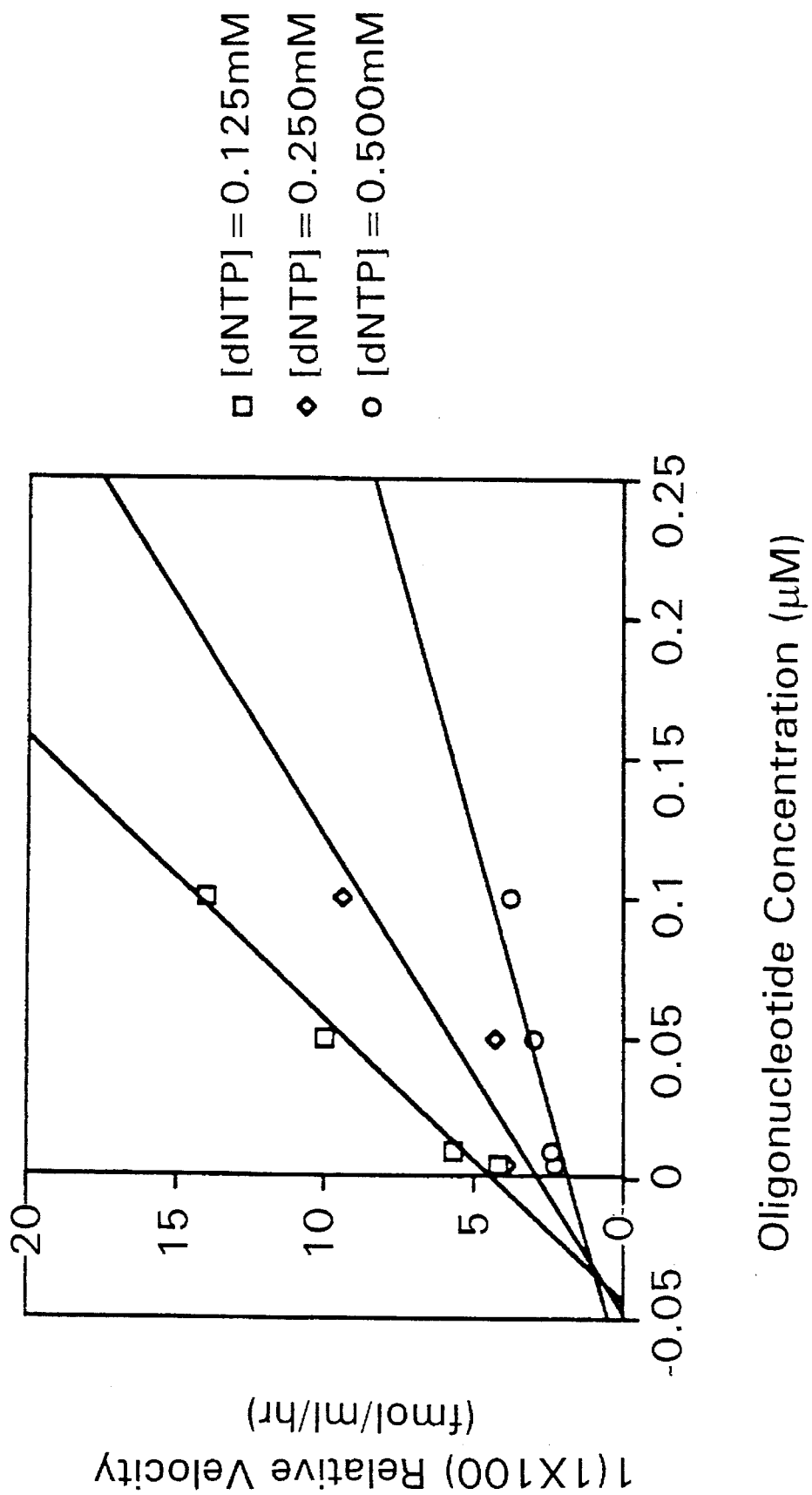
FIG. 8 shows a Dixon Plot of random oligonucleotide 1232 (SEQ. ID. NO. 41) obtained from kinetic analysis of inhibition of HIV-RT with respect to dNTP. The inhibition constant $K_i$ was determined by simultaneously varying dNTP (without dATP) concentrations at the same time as inhibitor (oligonucleotide 1232). The $K_i$ determination was performed at 0.125 mM, 0.25 mM and 0.5 mM dNTP concentrations with constant Primer-Template concentration of 0.2 pM. HIV-RT was used at 1 unit in each reaction. The reported values are the result of simultaneous independent duplicates determinations.

For competitive inhibitors, this type of analysis results in a family of lines which intersect at the point ($-K_i$, $1/V_{max}$), were $K_i$ is the inhibition constant and Vmax is the maximum velocity. Noncompetitive inhibitors give a family of lines intersecting at the point ($-K_i$, 0). The inhibition of HIV-1 RT by the PT containing random sequence oligonucleotide SEQ. ID. NO 41 (1232) is presented as an example in FIG. 8, which clearly indicates that oligonucleotide binding to HIV-RT precludes binding of natural substrate, suggesting a competitive mechanism of inhibition with respect to the template. The $K_i$ values were determined for all of the oligonucleotides tested and are presented in Table 7, which shows that the presence of the sulfur group in the backbone of an oligonucleotide greatly enhanced interaction between the oligonucleotide and the enzyme. The median inhibitory dose (ID$_{50}$) for these oligonucleotides were also calculated (see Table 7) based on the ability of these compounds to inhibit 10 nM of HIV-1 RT. The degree of enhancement of HIV-1 RT inhibition for shorter oligonucleotides (18 mers) with PT backbones was between one to three orders of magnitude greater than the analogous PD oligonucleotides (see Table 7). Other 18 mer PD oligonucleotide sequence motifs tested yielded similar results.

TABLE 7

In Vitro Inhibition of HIV-1 RT by PD and PT Oligonucleotides by ELISA

| Oligonucleotide[a] | Modification[b] | Ki (μM) | ID$_{50}$ (μM) |
|---|---|---|---|
| I100-00 | PD | 0.87 | 5.0 |
| I100-12 | PT | 0.0005 | 0.015 |
| I100-07 | PD | 0.137 | 2.5 |
| I100-21 | PT | 0.001 | 0.045 |
| 1173 | PD | >5.0 | >5.0 |
| 1174 | PT | 0.015 | 0.154 |
| 1229 (poly SdC) | PD | >5.0 | >5.0 |
| 1230 (poly SdC) | PT | 0.044 | 0.33 |
| 1231 (GATC) | PD | >5.0 | >5.0 |
| 1232 (GATC) | PT | 0.56 | 0.045 |

[a]Each pair of oligonucleotides contain the same sequence and differ only in the nature of their backbone linkage. Oligonucleotides 1229 and 1230 were poly SdC while the 1231 and 1232 oligonucleotides were a random sequence of all four bases (GATC).
[b]The backbone modifications are denoted as PD for phosphodiester and PT for phosphorothioate.

Inhibition of the Interaction of HIV-1 gp120 with Cellular CD4

The outer envelope glycoprotein gp120 of HIV-1 mediates viral attachment to the cell surface glycoprotein CD4 in the initial phase of HIV-1 infection (22). Table 8 shows the concentration of oligonucleotide needed to reduce CD4 bound gp120 by 50% (ID50 [gp120]). Additionally, the ability of I100-00, I100-07 and their PT versions to inhibit gp120/CD4 interactions by binding to immobilized CD4 was determined. I100-00, I100-07 and their PT versions were capable of preventing the interaction of gp120 with immobilized CD4 (ID$_{50}$[CD4], Table 8), however, the PT version of the oligonucleotides had ID$_{50}$ values 50 to 100 fold lower than the PD version (see Table 8). The PD versions of a set of 18 mer oligonucleotides had little to no measurable effects on the binding of gp120 with CD4. However, the PT versions of the oligonucleotides did yield measurable inhibitory activity. The 18 mer oligonucleotide (1174) interrupted gp120/CD4 interactions at approximately 10 fold lower concentrations than poly SdC$_{18}$ (1230). The random sequence 18 mer (1232) had no measurable activity (Table 8).

The addition of a sulfur group into the backbone of selected oligonucleotides enhanced anti-viral activity, over the matched phosphodiester compound, in culture and in-vitro for each assay system tested. The degree of enhanced anti-viral activity in culture was most pronounced (approximately 10 to 15 fold) for I100-12, when compared with I100-00 (Table 5). The degree of enhancement observed in vitro for some experiments reached 100 to 500 fold (Tables 7 and 8).

EXAMPLE 11

Inhibition of HCMV Activity

Several different oligonucleotides reduced HCMV titers in tissue culture. Each of the oligonucleotides contained a different percentage of guanosine residues and a different number of total nucleotides in the polymer. The results of this assay are depicted in Table 9. All oligonucleotides were capable of reducing viral titer in culture including G101-50 which contained only 53% G residues (16 out of 30 total nucleotides). In Table 9, the length and percent guanosine nucleotides is indicated for each oligonucleotide tested.

TABLE 8

In Vitro Inhibition of HIV-1 gp120 (125 ng/ml) Interaction with CD4 by PD and PT Oligonucleotides

| Oligonucleotide | back-bone[a] | ID$_{50}$[gp120] (µM) | ID$_{50}$[CD4] (µM) |
|---|---|---|---|
| I 100-00 | PD | 3.50 | 18.0 |
| I 100-12 | PT | 0.08 | 0.475 |
| I 100-07 | PD | 0.80 | 4.25 |
| I 100-21 | PT | 0.07 | 0.048 |
| 1173 | PD | >100.0 | >100.0 |
| 1174 | PT | 0.09 | 0.45 |
| 1229 (poly dC) | PD | >100.0 | >100.0 |
| 1230 (poly dC) | PT | 1.00 | 3.25 |
| 1231 (GATC) | PD | >100.0 | >50.0 |
| 1232 (GATC) | PT | >10.0 | >10.0 |

[a]Each pair of oligonucleotides contain the same sequence and differ only in the nature of their backbone linkage.
[b]The backbone modifications are denoted as PD for phosphodiester and PT for phosphorothioate.

TABLE 9

Oligonucleotide Inhibition of HCMV Activity Viral Yield in plaque forming units (PFU)

| [oligo] | oligonucleotide (% G) | | | | |
|---|---|---|---|---|---|
| | G101-50 (53%) 30 mer | G105-50 (80%) 31 mer | G106-50 (78%) 27 mer | G109-50 (65%) 29 mer | G113-50 (64%) 24 mer |
| None | 4.5 × 10$^3$ PFU | 4.5 × 10$^3$ PFU | 4.5 × 10$^3$ PFU | 4.5 × 10$^3$ PFU | 4.5 × 10$^3$ PFU |
| 20.0 µM | φ | 4.5 × 10$^1$ PFU | 2.5 × 10$^1$ PFU | 8.0 × 10$^1$ PFU | 3.5 × 10$^1$ PFU |
| 10.0 µM | 2.5 × 10$^1$ PFU | 1.8 × 10$^2$ PFU | 4.0 × 10$^1$ PFU | 4.5 × 10$^1$ PFU | 4.0 × 10$^1$ PFU |
| 1.0 µM | 7.0 × 10$^2$ PFU | 1.9 × 10$^2$ PFU | 6.0 × 10$^1$ PFU | 1.5 × 10$^2$ PFU | 5.0 × 10$^2$ PFU |
| 0.5 µM | 8.0 × 10$^2$ PFU | 2.7 × 10$^2$ PFU | 1.3 × 10$^2$ PFU | 3.0 × 10$^2$ PFU | 5.4 × 10$^{2-}$ PFU |

Figure 9A:
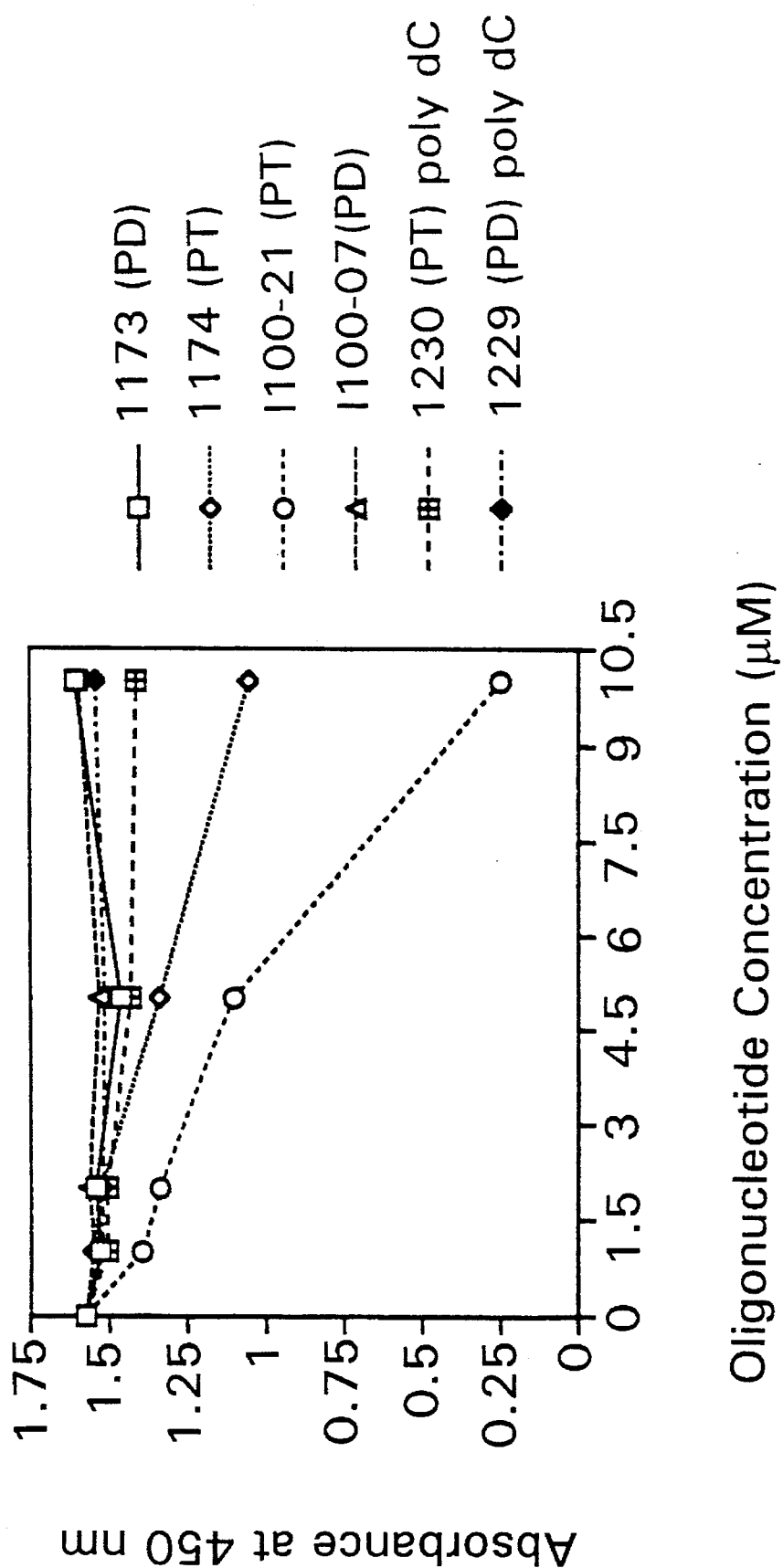
FIGS. 9A–9B show inhibition of binding of V3 loop specific Mabs to HIV-1 gp120 by phosphorothioate containing oligonucleotides. Matched sequence oligonucleotides with either phosphodiester (PD) or phosphorothioate (PT) backbones were assayed for their ability to inhibit the interaction of V3 loop specific Mabs with the gp120 molecule: SEQ. ID. NOs. 31 (1173) and 32 (1174); SEQ ID. NOs. 24 (I100-07) and 39 (I100-21); or SEQ. ID. NOs. 42 (1229) and 43 (1230). To do this immobilized gp120 was preincubated with oligonucleotides before washing and the addition of Mab NEA 9284 (panel A) or Mab NEA 9301 (panel B).
Figure 9B:
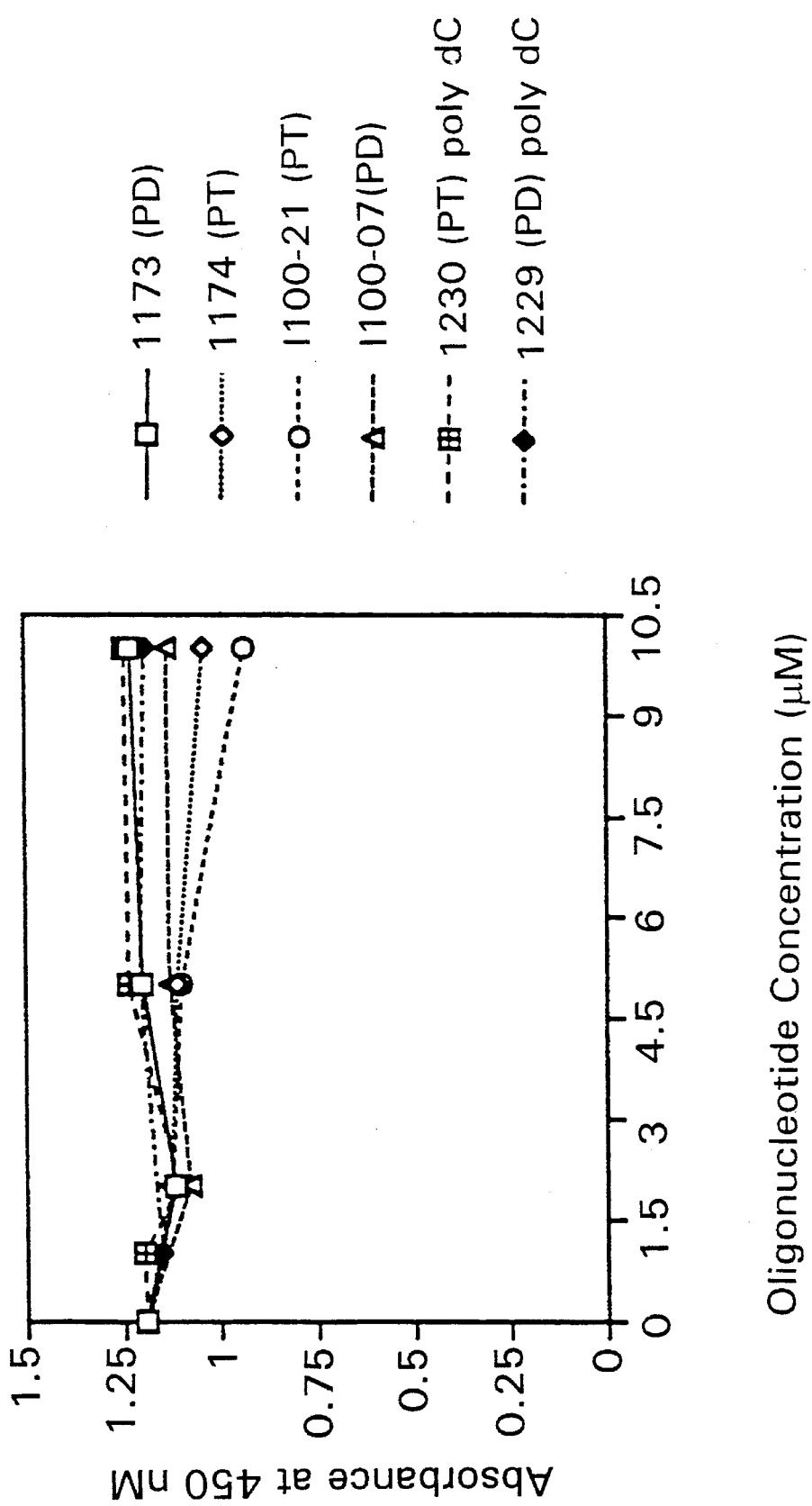

FIG. 9A shows that in interactions with the V3 loop using an additional V3 loop specific murine Mab, NEA-9284, that PT oligonucleotides were able to inhibit binding of NEA-9284 to gp120. The presence of bound gp120 specific Mab was verified using a HRP-labeled goat-a-mouse antibody. The ID$_{50}$ for the most active oligonucleotide (I100-21) was approximately 4 to 7 uM. This concentration was approximately 10 to 30 fold higher than the ED$_{50}$ value for this oligonucleotide against HIV-1 in culture (Table 5). Oligonucleotide effects on two another V3 loop specific murine Mabs, NEA-9301 (FIG. 9B) and 9305, were minimal. The PD oligonucleotides tested did not inhibit the binding of any Mab to gp120. Oligonucleotides were preincubated with immobilized gp120 before the addition of the V3 loop specific Mabs.

In NIH3T3 cells chronically infected with FMLV, oligonucleotides (FIG. 1) were capable of inhibiting virus production. However, oligonucleotides controls in this experiment were capable of inhibiting virus production in culture.

EXAMPLE 12

In Vitro Enzymatic Assays

Figure 4:
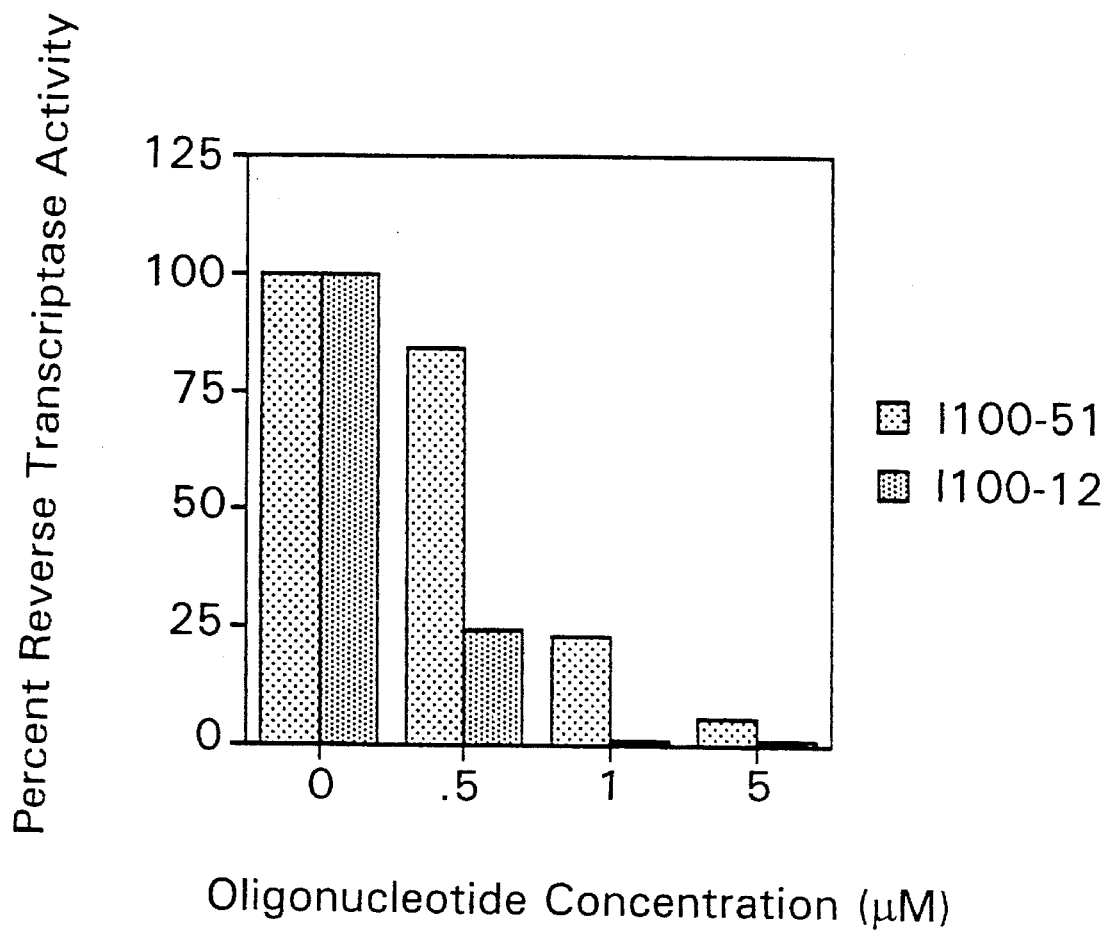
FIG. 4 shows the culture media taken from NIH3T3 cells chronically infected with FMLV was mixed with various concentrations of I100-51 or I100-12 (fully phosphorothioate version of I100-00). The mixtures were then assayed for the presence of viral reverse transcriptase. The data is presented as a percent of measurable reverse transcriptase in culture medium not treated with oligonucleotide.

Culture media containing FMLV reverse transcriptase (RT) was mixed with various concentrations of I100-51 or I100-12, the phosphodiester backbone of I100-51 having been modified to a phosphorothioate backbone. Reverse transcriptase was measured as described in Example 7. FIG. 4 shows that both oligonucleotides were capable of inhibiting the RT enzyme. Inhibitory concentrations for 50% reduction in RT activity was between 0.5 to 1 µM for I100-51 and less than 0.5 uM for I100-12.

Figure 5A:
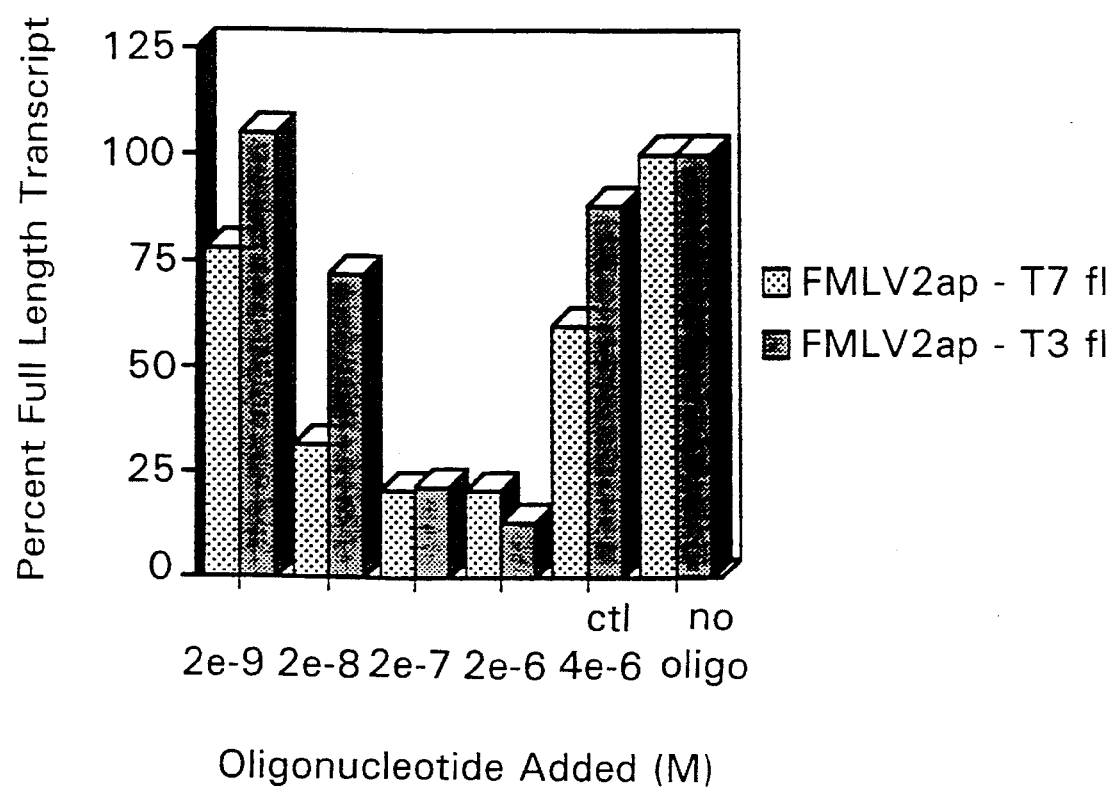
FIGS. 5A–5C show the radio-labelled ($^{32}$P) full-length or truncated mRNA transcripts were analyzed by polyacrylamide gel electrophoresis, and then quantitated by cutting out the specific transcript and measuring the radioactivity in a scintillation counter.
Figure 5B:
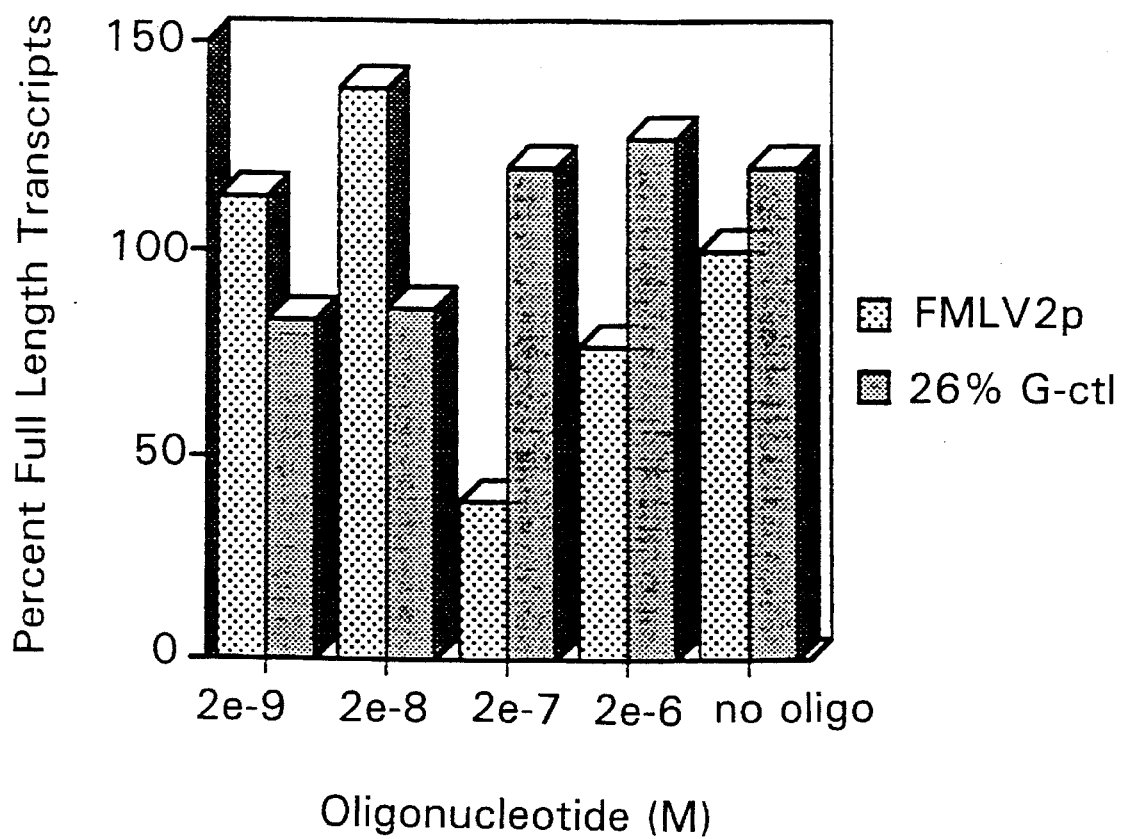
Figure 5C:
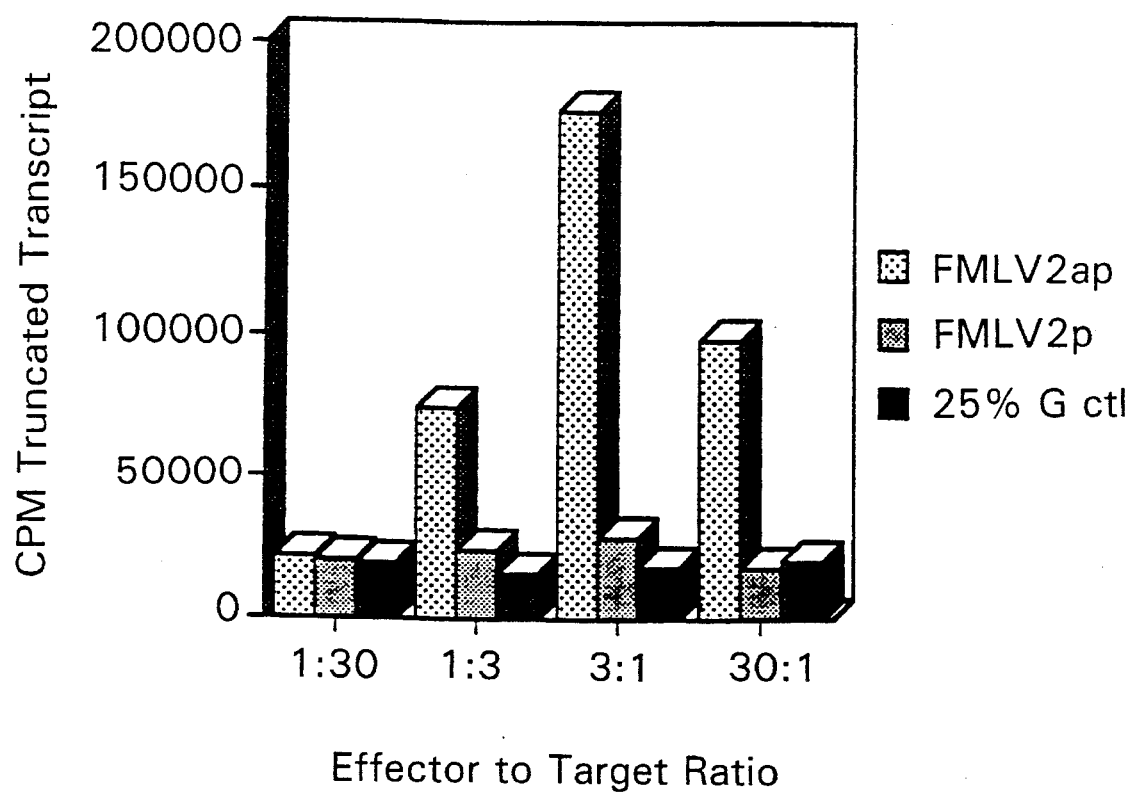

The I100-51 (FMLV2ap), attenuated full length transcription directed by either the T7 or T3 polymerases (FIG. 5a). As can be seen in FIG. 1, full length transcripts directed by the T7 promoter would be 131 bases long while full length transcripts directed by the T3 promoter would be 171 bases long (position of the Dde I site relative to the mRNA start site). The sequence isomer of I100-51 (I100-01=FMLV2p), designed parallel to the target strand was also capable of significantly inhibiting transcription from the T7 promoter (FIG. 5b). However, only the anti-parallel triple helix forming oligonucleotide FMLV2ap inhibited via attenuation of transcription as can be seen in the build up of a truncated transcript in the reaction mix (FIG. 5C). The truncated transcript analyzed in FIG. 5C was approximately 63 bases long and matched the predicted size fragment when p275A was used as a template (T7 promoter). G101-50 (53% G) inhibited T7, but not T3 directed, transcription by a mechanism other than attenuation (FIG. 5A) since no truncated transcripts were observed when this oligonucleotide was used alone. I100-11 (26% G) increased the level of specific transcripts directed by the T7 promoter (FIG. 4b).

In experiments designed to monitor inhibition of transcription initiation of the HSV-1 IE175 promoter, using oligonucleotides, both specific and control G-Rich oligonucleotides were capable of inhibiting eukaryotic transcription when a HeLa cell extract system was used. The oligonucleotides used were B133-54; B133-55 and B107-51 as specific inhibitors via potential triple helix mechanism of action and G101-50 and I100-11 as the low G-content control oligonucleotides.

The present invention demonstrates anti-viral activity in tissue culture assays for several G-Rich oligonucleotides against HSV-2, HIV-1, HCMV and FMLV. In addition, G-Rich oligonucleotides specifically inhibited the bacterial RNA polymerase enzymes T7 and T3, the FMLV reverse transcriptase enzyme and eukaryotic RNA polymerase.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The oligonucleotides, compounds, methods, procedures and techniques described herein are presently representative of preferred embodiments, are intended to be exemplary and are not intended as limitations on the scope. Changes therein and other uses will occur to those skilled in the art which are encompassed within the spirit of the invention or defined by the scope of the appended claims.

What is claimed is:

1. A method of inhibiting the production of a human immunodeficiency virus in cultured cells comprising contacting said virus with an oligonucleotide selected from the group consisting of SEQ ID NOS: 2–27, 29 and 31–39.

2. The method of claim 1, wherein said oligonucleotide is capped at the 3' terminus with a modifier selected from the group consisting of propylamine, polyamine, poly-L-lysine and cholesterol.

3. The method of claim 2, wherein the modifier is propylamine.

4. The method of claim 1, wherein said oligonucleotide is capped at the 5' terminus with a modifier selected from the group consisting of propylamine, polyamine, poly-L-lysine and cholesterol.

5. The method of claim 4, wherein the modifier is propylamine.

6. The method of claim 1, wherein said oligonucleotide comprises at least one phosphodiester linkage.

7. The method of claim 1, wherein said oligonucleotide comprises at least one phosphorothioate linkage.

8. The method of claim 1, wherein said oligonucleotide is selected from the group consisting of SEQ ID NOS: 2, 4–27, 29 and 31–39.

9. The method of claim 1 wherein said oligonucleotide consists of at least 50% guanosine bases.

10. A method of inhibiting the production of a human immunodeficiency virus in cultured cells comprising contacting said virus with the oligonucleotide of SEQ ID NO: 33.

11. A method of inhibiting the replication of a human immunodeficiency virus in cultured cells comprising contacting said virus with an oligonucleotide selected from the group consisting of SEQ ID NOS: 2–27, 29 and 31–39, wherein said oligonucleotide is capped at the 3' terminus and/or at the 5' terminus with a modifier independently selected from the group consisting of propylamine, polyamine, poly-L-lysine and cholesterol.

12. A method of inhibiting the replication of a human immunodeficiency virus in cultured cells comprising contacting said virus with the oligonucleotide of SEQ ID NO: 33, wherein said oligonucleotide is capped at the 3' terminus and/or at the 5' terminus with a modifier independently selected from the group consisting of propylamine, polyamine, poly-L-lysine and cholesterol, and wherein said oligonucleotide comprises at least one phosphodiester linkage and/or at least one phosphorothioate linkage.

* * * * *